United States Patent
Kasid et al.

(10) Patent No.: US 7,253,272 B2
(45) Date of Patent: Aug. 7, 2007

(54) GENE BRCC-2 AND DIAGNOSTIC AND THERAPEUTIC USES THEREOF

(75) Inventors: Usha Kasid, Rockville, MD (US); Prafulla Gokhale, Oak Hill, VA (US); Deepak Kumar, Arlington, VA (US); Constantinos Broustas, Arlington, VA (US); Imran Ahmad, Wadsworth, IL (US); Anatoly Dritschilo, Bethesda, MD (US); Aquilur Rahman, Potomac, MD (US)

(73) Assignee: Georgetown University, Washington, DC (US)

( * ) Notice: Subject to any disclaimer, the term of this patent is extended or adjusted under 35 U.S.C. 154(b) by 38 days.

(21) Appl. No.: 10/679,865

(22) Filed: Oct. 6, 2003

(65) Prior Publication Data

US 2004/0115714 A1    Jun. 17, 2004

Related U.S. Application Data

(63) Continuation of application No. PCT/US02/10848, filed on Apr. 8, 2002.

(60) Provisional application No. 60/281,796, filed on Apr. 6, 2001.

(51) Int. Cl.
  *C07H 21/02*  (2006.01)
  *C07H 21/04*  (2006.01)
(52) U.S. Cl. .................. 536/23.1; 536/23.5; 536/24.31
(58) Field of Classification Search ................ 536/23.1
  See application file for complete search history.

(56) References Cited

U.S. PATENT DOCUMENTS

| | | |
|---|---|---|
| RE30,985 E | 6/1982 | Cartaya |
| 4,399,216 A | 8/1983 | Axel et al. |
| 4,551,433 A | 11/1985 | DeBoer |
| 4,560,655 A | 12/1985 | Baker |
| 4,657,866 A | 4/1987 | Kumar |
| 4,745,051 A | 5/1988 | Smith et al. |
| 4,767,704 A | 8/1988 | Cleveland et al. |
| 4,777,127 A | 10/1988 | Suni et al. |
| 4,816,567 A | 3/1989 | Cabilly et al. |
| 4,837,148 A | 6/1989 | Cregg |
| 4,889,806 A | 12/1989 | Olson et al. |
| 4,927,762 A | 5/1990 | Darfler |
| 4,929,555 A | 5/1990 | Cregg et al. |
| 4,959,314 A | 9/1990 | Mark et al. |
| 5,013,830 A | 5/1991 | Ohtsuka et al. |
| 5,091,309 A | 2/1992 | Schlesinger et al. |
| 5,149,655 A | 9/1992 | McCabe et al. |
| 5,149,797 A | 9/1992 | Pederson et al. |
| 5,185,440 A | 2/1993 | Davis et al. |
| 5,206,152 A | 4/1993 | Sukhatme |
| 5,217,879 A | 6/1993 | Huang et al. |
| 5,219,740 A | 6/1993 | Miller et al. |
| 5,219,773 A | 6/1993 | Dunn |
| 5,403,711 A | 4/1995 | Walder et al. |
| 5,422,120 A | 6/1995 | Kim |
| 5,491,133 A | 2/1996 | Walder et al. |
| 5,514,758 A | 5/1996 | Muller et al. |
| 5,530,101 A | 6/1996 | Queen et al. |
| 5,536,821 A | 7/1996 | Agrawal et al. |
| 5,541,306 A | 7/1996 | Agrawal et al. |
| 5,550,111 A | 8/1996 | Suhadolnik et al. |
| 5,563,253 A | 10/1996 | Agrawal et al. |
| 5,565,350 A | 10/1996 | Kmiec |
| 5,565,552 A | 10/1996 | Magda et al. |
| 5,567,810 A | 10/1996 | Weis et al. |
| 5,571,799 A | 11/1996 | Tkachuk et al. |
| 5,574,142 A | 11/1996 | Meyer, Jr. et al. |
| 5,580,859 A | 12/1996 | Felgner et al. |
| 5,585,089 A | 12/1996 | Queen et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,597,696 A | 1/1997 | Linn et al. |
| 5,610,018 A | 3/1997 | Di Fiore et al. |
| 5,625,050 A | 4/1997 | Beaton et al. |
| 5,641,670 A | 6/1997 | Treco et al. |
| 5,652,355 A | 7/1997 | Metelev et al. |
| 5,700,922 A | 12/1997 | Cook |
| 5,776,745 A | 7/1998 | Ketner et al. |
| 5,801,154 A | 9/1998 | Baracchini et al. |
| 5,928,939 A * | 7/1999 | Eriksson et al. ............ 435/325 |
| 5,939,598 A | 8/1999 | Kucherlapati et al. |
| 5,958,773 A | 9/1999 | Monia et al. |
| 6,333,314 B1 | 12/2001 | Kasid et al. |

(Continued)

FOREIGN PATENT DOCUMENTS

| | | |
|---|---|---|
| EP | 36776 A2 | 9/1981 |
| EP | 0 127 839 A2 | 12/1984 |
| EP | 0 155 476 A1 | 9/1985 |
| EP | 0 244 234 A2 | 11/1987 |
| EP | 0 345 242 A2 | 12/1989 |
| EP | 0 415 731 A2 | 3/1991 |
| EP | 0 524 968 B1 | 3/1993 |

(Continued)

OTHER PUBLICATIONS

Bennett et al. (Circulation, 1995, 92(7):1981-1993).*

(Continued)

*Primary Examiner*—Shanon Foley
*Assistant Examiner*—Sean E Aeder
(74) *Attorney, Agent, or Firm*—DLA Piper US LLP

(57) ABSTRACT

A gene that is a modulator of tumor growth and metastasis in certain cancer types is provided. This gene and corresponding polypeptide have diagnostic and therapeutic application for detecting and treating cancers that involve expression of BRCC2 such as breast cancer and lung cancer.

4 Claims, 4 Drawing Sheets

FOREIGN PATENT DOCUMENTS

Figure 3:
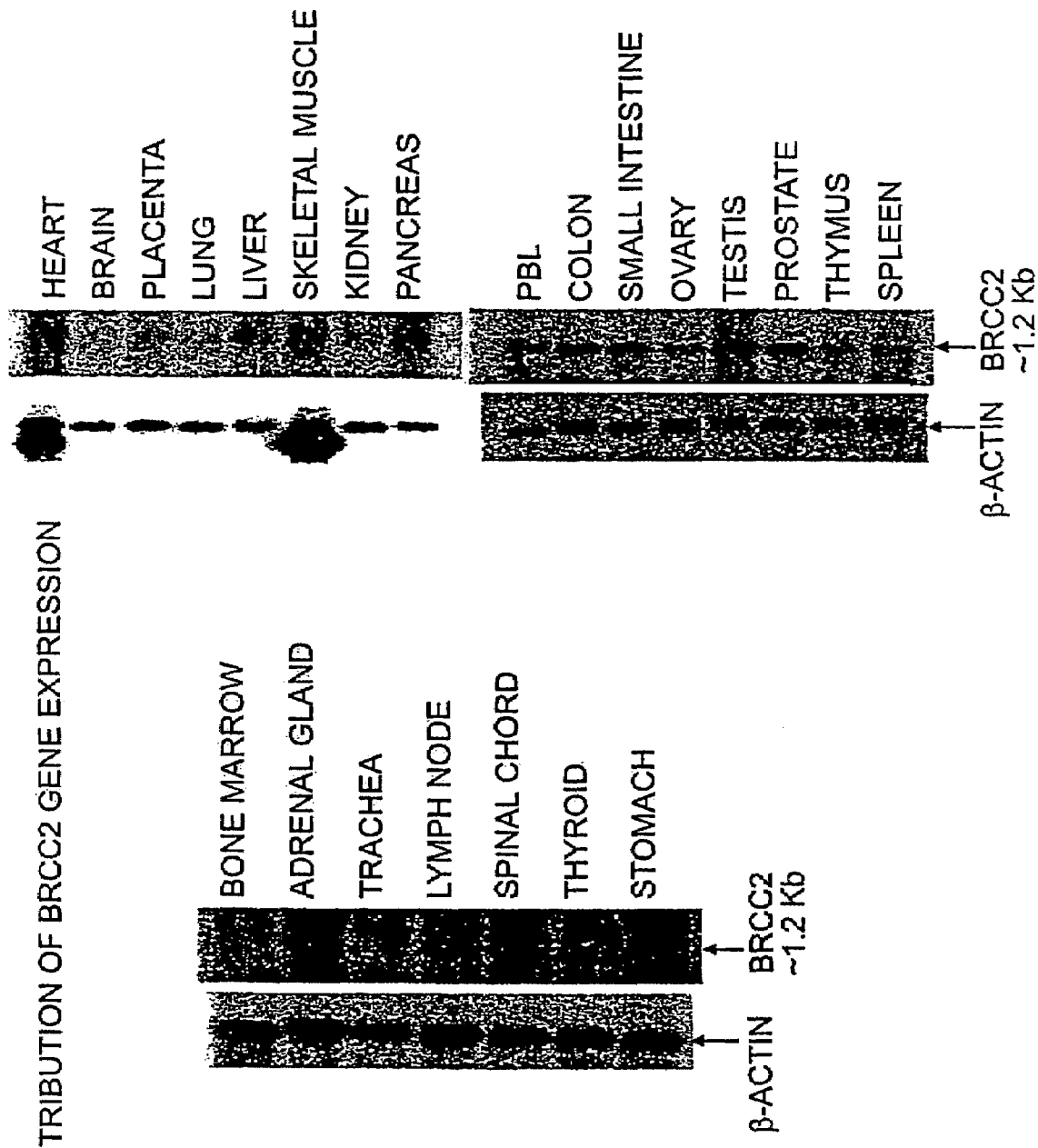

| EP | 1074617 A2 | 2/2001 |
|---|---|---|
| GB | 2 200 651 A | 8/1988 |
| WO | WO 87/00195 A1 | 1/1987 |
| WO | WO 90/03430 A1 | 4/1990 |
| WO | WO 90/07936 A1 | 7/1990 |
| WO | WO 90/11092 A1 | 10/1990 |
| WO | WO 91/00357 A1 | 1/1991 |
| WO | WO 91/02805 A2 | 3/1991 |
| WO | WO 91/10741 A1 | 7/1991 |
| WO | WO 91/14445 A1 | 10/1991 |
| WO | WO 92/05266 A2 | 4/1992 |
| WO | WO 92/10578 A1 | 6/1992 |
| WO | WO 92/11033 A1 | 7/1992 |
| WO | WO 93/03769 A1 | 3/1993 |
| WO | WO 93/04170 A1 | 3/1993 |
| WO | WO 93/06248 A1 | 4/1993 |
| WO | WO 93/09239 A1 | 5/1993 |
| WO | WO 93/10218 A1 | 5/1993 |
| WO | WO 93/11230 A1 | 6/1993 |
| WO | WO 93/19191 A1 | 9/1993 |
| WO | WO 93/25234 A1 | 12/1993 |
| WO | WO 93/25698 A1 | 12/1993 |
| WO | WO 94/02602 A1 | 2/1994 |
| WO | WO 94/03622 A1 | 2/1994 |
| WO | WO 94/12649 A2 | 6/1994 |
| WO | WO 94/15645 A1 | 7/1994 |
| WO | WO 94/21792 A2 | 9/1994 |
| WO | WO 94/23697 A1 | 10/1994 |
| WO | WO 94/28938 A1 | 12/1994 |
| WO | WO 95/00655 A1 | 1/1995 |
| WO | WO 95/07994 A2 | 3/1995 |
| WO | WO 95/11984 A2 | 5/1995 |
| WO | WO 95/13796 A1 | 5/1995 |
| WO | WO 95/27044 A1 | 10/1995 |
| WO | WO 95/27069 A1 | 10/1995 |
| WO | WO 95/30763 A2 | 11/1995 |
| WO | WO 96/30498 A1 | 10/1996 |
| WO | WO 96/33735 A1 | 10/1996 |
| WO | WO 96/34096 A1 | 10/1996 |
| WO | WO 98/24893 A2 | 6/1998 |
| WO | WO 00/00157 A2 | 1/2000 |
| WO | WO 02/059337 A1 | 8/2002 |
| WO | WO 02/081639 A2 | 10/2002 |
| WO | WO 02/081640 A2 | 10/2002 |
| WO | WO 02/081641 A2 | 10/2002 |
| WO | WO 02/081642 A2 | 10/2002 |

OTHER PUBLICATIONS

Birren et al (*Homo sapiens* chromosome 11 clones RP11-85D24 map 11, Apr. 22, 2000).*
Riedel et al. (Eur. J. Immunol., 23, 3146-3150, 1993).*
Patel et al (Molecular Medicine, 1997, 3(10):674-685).*
Patel et al (Molecular Medicine, 1997, 3 (10):674-685).*
Gura (Science, 1997, 278:1041-1042.).*
U.S. Appl. No. 60/264,062, filed Jan. 26, 2001, Kumar et al.
U.S. Appl. No. 60/281,780, filed Apr. 6, 2001, Kasid et al.
U.S. Appl. No. 60/382,031, filed May 22, 2002, Gokhale et al.
U.S. Appl. No. 60/371,126, filed Apr. 10, 2002, Kasid et al.
U.S. Appl. No. 60/281,779, filed Apr. 6, 2001, Kasid et al.
U.S. Appl. No. 60/281,785, filed Apr. 6, 2001, Kasid et al.
U.S. Appl. No. 60/371,116, filed Apr. 10, 2002, Kasid et al.
U.S. Appl. No. 60/281,796, filed Apr. 6, 2001, Kasid et al.
U.S. Appl. No. 10/056,210, filed Jan. 28, 2002, Kasid et al.
U.S. Appl. No. 10/411,931, filed Apr. 10, 2003, Kasid et al.
U.S. Appl. No. 10/411,930, filed Apr. 10, 2003, Kasid et al.
U.S. Appl. No. 10/443,273, filed May 22, 2003, Gokhale et al.
U.S. Appl. No. 10/627,571, filed Jan. 28, 2002, Kasid et al.
U.S. Appl. No. 10/679,561, filed Oct. 6, 2003, Kasid et al.
U.S. Appl. No. 10/679,865, filed Oct. 6, 2003, Kasid et al.
U.S. Appl. No. 10/680,313, filed Oct. 6, 2003, Kasid et al.
U.S. Appl. No. 10/679,580, filed Oct. 6, 2003, Kasid et al.
Agrawal, *Biochimica et Biophysica Acta*, 1489(1), 53-68 (1999).
Altschul et al., *Nucleic Acids Research*, 25(17), 3389-3402 (1997).
Alvarez et al., *The Journal of Biological Chemistry*, 266(23), 15277-15285 (1991).
Ashkenazi et al., *Science*, 281(5381), 1305-1308 (1998).
Barba et al., *Journal of Neurosurgery*, 79(5), 729-735 (1993).
Baccarini et al., *The Journal of Biological Chemistry*, 266(17), 10941-10945 (1991).
Bain et al., *Gene Therapy*, 1(S68), (1994).
Ballance et al., *Biochemical and Biophysical Research Communications*, 112(1), 284-289 (1983).
Barnes et al., *Analytical Biochemistry*, 102(2), 255 (1980).
*Basic and Clinical Immunology*, 217-262 (Sites and Terr eds., Appleton & Lange, Norwalk, CT 1991).
Beach et al., *Nature*, 300(5894), 706-709 (1981).
Belyavsky et al., *Nucleic Acids Research* 17(8), 2919-2932 (1989).
Berkner, *BioTechniques*, 6(7), 616-629 (1988).
Berns et al., *Annals of The New York Academy of Sciences*, 772, 95-104 (1995).
Bertin et al., *Proceedings of the National Academy of Sciences of the United States of America*, 94(4), 1172-1176 (1997).
Blundell et al., *Nature*, 326(6111), 347-352 (1987).
Boldin et al., *Cell*, 85(6), 803-815 (1996).
Boshart et al., *Cell*, 41(2), 521 (1985).
Bowie et al., *Science*, 247(4948), 1306-1310 (1990).
Branch et al., *Trends in Biochemical Sciences*, 23(266), 45-50 (1998).
Bruder et al., *Genes & Development*, 6(4), 545-556 (1992).
Bruhn et al., *Proceedings of the National Academy of Sciences of the United States of America*, 89, 2307-2311 (1992).
Buruham et al., *American Journal of Hospital Pharmacy* 51(2), 210-218 (1994).
Caillaud et al., *European Journal of Neuroscience*, 5(10), 1287-1291 (1993).
Caplen et al., *Proceedings of the National Academy of Sciences of the United States of America*, 98(17) 9742-47 (2001).
Carbonell et al., *Gene*, 73(2), 409-418 (1988).
Carroll et al., *The Journal of Biological Chemistry*, 266(23) 14964-14969 (1991).
Carprino et al., *The Journal of Organic Chemistry*, 37, 3404-3409 (1972).
Chang et al., *Nature*, 275(5681), 617-624 (1978).
Chin, "On the preparation and utilization of isolated and purified oligonucleotides", Katherine R. Everett Law Library of the University of North Carolina, Mar. 2002 (on a CD).
Chinnaiyan et al., *The Journal of Biological Chemistry*, 271(9) 4961-4965 (1996).
Chiou et al., *Virology*, 244(1), 108-118 (1998).
Chothia et al., *Journal of Molecular Biology*, 196(4) 901-917 (1987).
Chung et al., *Proceedings of the National Academy of Sciences of the United States of America*, 88(11), 4981-(1991).
Cleland et al., *Critical Reviews in Therapeutic Drug Carrier Systems*, 10(4), 307-377 (1993).
Connelly, *Human Gene Therapy*, 6(2), 185-193 (1995).
Corpet et al., *Nucleic Acids Research.*, 16(22), 10881-10890 (1988).
Cozens et al., *Journal of Molecular Biology*, 206(2), 261-280 (1989).
Cregg et al., *Molecular and Cellular Biology*, 5(12), 3376-3385 (1985).
Crooke, *Biochimica et Biophysica Acta*, 1489(1) 31-44 (1999).
Cunningham et al., *Science*, 244(108), 1081-1085 (1989).
Curiel et al., *Human Gene Therapy*, 3(2), 147-154 (1992).
Darzynkiewicz et al., *Cytometry*, 13(8), 795-808 (1992).
Das et al., *Journal of Bacteriology*, 158(3), 1165-1167 (1984).
Davidow et al., *Current Genetics*, 10(1), 39-48 (1985).
Davis, *The New Biologist*, 2(5), 410-419 (1990).
Davis et al., *Enzyme Engineering*, 4, 169-73 (1978).
Dayhoff et al., *Atlas of Protein Sequence and Strucure*, 5(Supplement 3), 345-352 (1978).
De Bohr et al., *Proceedings of the National Academy of Sciences of the United States of America*, 80(1), 21-25 (1983).

De Louvencourt et al., *Journal of Bacteriology*, 154(2), 737-742 (1983).
Dent et al., *Science*, 257(5075), 1404-1407 (1992).
Devary et al., *Cell*, 71, 1081-1091 (1992).
De Vos et al., *Science*, 255(5042), 306-312 (1992).
Dijkema et al., *The EMBO Journal*, 4(3), 761 (1985).
Dinchuk et al., *The Journal of Biological Chemistry*, 275(50), 39543-39554 (2000).
Downing et al., *Cell*, 85(4), 597-605 (1996).
Earl et al., *Proceedings of the National Academy of Sciences of the United States of America*, 83(11), 3659-3663 (1986).
Elbashir et al., *Nature*, 411(6836), 494-98 (2001).
Fabian et al., *Molecular and Cellular Biology*, 13(11), 7170(1993).
Federoff et al., *Proceedings of the National Academy of Sciences of the United States of America*, 89(5), 1636-40 (1992).
Felger et al., *Human Gene Therapy*, 7(15), 1791-1793 (1996).
Fiermonte et al, *The Journal of Biological Chemistry*, 276(11), 8225-8230 (2001).
Finco et al., *The Journal of Biological Chemistry*, 268(24), 17676-17679 (1993).
Fink et al., *Annual Review of Neuroscience*, 19, 265-87 (1992).
Flotte et al., *Proceedings of the National Academy of Sciences of the United States of America*, 90(22), 10613-10617 (1993).
Friden et al., *Science*, 259, 373-377 (1993).
Friesen et al., *The Molecular Biology of Baculoviruses*, 31-49 (1986).
Gaillardin et al., *Current Genetics*, 10, 49-58 (1985).
Galfre et al., *Methods in Enzymology; Immunochemical Techniques*, 73, 3-46 (1981).
Gardner et al., *The Journal of Biological Chemistry*, 268(24) 1789617901(1993).
Gille et al., *Nature*, 358(6385), 414-417 (1992).
Gleeson et al., *The Journal of General Microbiology*, 132(12), 3459-3465 (1986).
Goeddel et al., *Nature*, 281(5732), 544 (1979).
Goeddel et al., *Nucleic Acids Research*, 8(18), 4057-4074 (1980).
Gokhale et al., *Gene Therapy*, 4(12), 1289-1299 (1997).
Gokhale et al., *Antisense & Nucleic Acid Drug Development*, 9(2), 191-201 (1999).
Goltsev et al., *The Journal of Biological Chemistry*, 272(32), 19641-19644 (1997).
Gonzalez et al., *Current Opinion in Biotechnology*, 9(6), 624-631 (1998).
Gorman et al., *Proceedings of the National Academy of Sciences of the United States of America*, 79(22), 6777-6781 (1982).
Goruppi et al., *FEBS Letters*, 415(1), 59-63 (1997).
Green et al., *Science*, 281(5381), 1309-1312 (1998).
Griffith et al., *The Journal of Immunology*, 161(6), 2833-2840 (1998).
Guzman et al., *Circulation Research*, 73(6), 1202-1207 (1993).
Guzman et al., *Circulation*, 88(6), 2838-2848 (1993).
Ham et al., *Methods in Enzymology*, 58, 44-93 (1979).
Han et al., *American Journal of Respiratory Cell and Molecular Biology*, 11(3), 270-278 (1994).
Heidecker et al., *Molecular and Cellular Biology*, 10(6), 2503-2512 (1990).
Heidecker et al., *Advances in Cancer Research*, 58, 53-73 (1992).
Heo et al., *Cancer Research*, 49(18), 5167-5175 (1989).
Higgins et al., *Computer Applications in the Biosciences*, 8(2), 189-191 (1992).
Hinnen et al., *Proceedings of the National Academy of Sciences*, 75(4), 1929-1933 (1978).
Horrevoets et al., *Blood*, 93(10), 3418-3431 (1999).
Houldworth et al., *Proceedings of the National Academy of Sciences of the United States of America*, 85(1), 377-371 (1988).
Howe et al., *Cell*, 71(2), 335-342 (1992).
Hu et al., *Virology*, 227(2), 295-304 (1997).
Hu et al., *The Journal of Biological Chemistry*, 272(15), 9621-9624 (1997).
Hu et al., *The Journal of Biological Chemistry*, 272(28), 17255-17257 (1997).
Inbal et al., *Nature*, 390(6656), 180-184 (1997).
Irmier et al., *Nature*, 368(6638), 190-195 (1997).
Ito et al., *Journal of Bacteriology*, 153(1), 163-168 (1983).
Jaffe et al., *Nature Genetics*, 1(5), 372-378 (1992).
Jolly, *Cancer Gene Therapy*, 1(1), 51-64 (1994).
Jones et al., *Nature*, 321(6069), 522-525 (1986).
Kaplitt, *Nature Genetics*, 8(2), 148-154 (1994).
Kasid et al., *Science*, 238(4818), 1039-1041 (1987).
Kasid et al., *Science*, 243(4896), 1354-1356 (1989).
Kasid et al., *Advances in Cancer Research*, 61, 195-233 (1993).
Kasid et al., *Nature*, 382(6594), 813-816 (1996).
Kasid et al., *Molecular and Cellular Biochemistry*, 173(1&2), 193-197 (1997).
Kasid et al., *Apoptosis Genes*, Kluwer Academic Publishers, MA (eds. Potten. Booth, & Wilson), 85-118 (1998).
Kass-Bisler et al., *Proceedings of the National Academy of Sciences of the United States of America*, 90(24), 11498-11502 (1993).
Kataoka et al., *The Journal of Immunology*, 161(8), 3936-3942 (1998).
Kelly et al., *The EMBO Journal*, 4(2), 475-479 (1985).
Kelson et al., *Biochimica Et Biophysica Acta*, 1335(1-2), 99-110 (1997).
Kettleborough et al., *Protein Engineering.*, 4(7), 773-83 (1991).
Kimura, *Human Gene Therapy*, 5(7), 845-852 (1994).
Kissil et al., *The EMBO Journal*, 18(2), 353-362 (1999).
Kizaka-Kondoh et al., *Molecular and Cellular Biology*, 12(11), 50780-5086 (1992).
Koide et al., *Proceedings of the National Academy of Sciences of the United States of America*, 90(18), 8683 (1993).
Kolarov et al., *The Journal of Biological Chemistry*, 265(21), 12711-12716 (1990).
Kolch et al., *Nature*, 349(6308), 426-428 (1991).
Kolls et al., *Proceedings of the National Academy of Sciences of the United States of America*, 91(1), 9215-219 (1994).
Korioth et al., *Gene*, 150(2), 395-399 (1994).
Krug et al., *Methods in Enzymology; Guide to Molecular Cloning Techniques*, 152, 316-325 (1987).
Kumar et al., *The Journal of Biological Chemistry*, 275(4) 2973-2978 (2000).
Kunze et al., *Journal of Basic Microbiology*, 25(2), 141-144 (1985).
Kurtz et al., *Molecular and Cellular Biology*, 6(1), 142 (1986).
Kyriakis et al., *Nature*, 358(6385), 417-421 (1992).
Lawson et al., *The Journal of Biological Chemistry*, 263(29), 14812-14818 (1988).
Lebacq-Verheyden et al., *Molecular and Cellular Biology*, 8(8), 3129 (1988).
Lee et al., *The Journal of Biological Chemistry*, 266(16), 10351-10357 (1991).
Lennon et al., *Genomics*, 33(1), 151-152 (1996).
Levero et al., *Gene*, 101(2), 195-202 (1991).
Li et al., *Human Gene Therapy*, 4(4), 403-409 (1993).
Li et al., *Proceedings of the National Academy of Sciences*, 92(20), 9247-9251 (1993).
Liang et al., *Science*, 257(5072), 967-971 (1992).
Lim et al., *Gene*, 255, 35-42 (2000).
Luciakova et al., *Biochemical Journal*, 352(2), 519-523 (2000).
Luckow et al., *Bio/Technology*, 6(1), 47-55 (1988).
MacDonald et al., *Molecular and Cellular Biology*, 13(11), 6615-6620 (1993).
Maeda et al., *Nature*, 315(6020), 592-594 (1985).
Marshall et al., *Cell*, 80(2), 179-185 (1995).
Martens et al., *Analytical Biochemistry*, 273(1), 20-31 (1999).
Martin et al., *DNA*, 7(2), 99-106 (1988).
Marzo et al., *The Journal of Experimental Medicine*, 187(8), 1261-1271 (1998).
Mendelson et al., *Virology*, 166, 154-165 (1988).
Merrifield et al., *Journal of the American Chemical Society*, 85, 2149-2154 (1963).
Miller et al., *Genetic Engineering*, 8, 277-279 (1986) (Setlow et al. ed.).
Miller, *Annual Review of Microbiology*, 42, 177-199 (1988).
Milner et al., *Nature Biotechnology*, 15, 537-541 (1997).
Milstein et al., *Nature*, 256(5517), 495-497 (1975).
Miyajima et al., *Gene*, 58(2&3), 273-281 (1987).
Monia et al., *Nature Medicine*, 2(6), 668-675 (1996).
Morimoto et al., *The Journal of Immunology*, 147(8), 2609-2616 (1991).
Morrison et al., *The Journal of Biological Chemistry*, 268(23), 17309-17316 (1993).
Morrison et al., *Proceedings of the National Academy of Sciences of the United States of America*, 81(21), 6851-6855 (1984).
Morrison et al., *Advances in Immunology*, 44, 65-92 (1988).
Muzio et al., *Cell*, 85(6), 817-827 (1996).

Nakai et al., *Genomics*, 14, 897-911 (1992).
Nakamura et al., *The Journal of Biological Chemistry*, 274(32), 22476-22483 (1999).
Neckelmann et al., *Proceedings of the National Academy of Sciences of the United States of America*, 84(21), 7580-7584 (1987).
Nicoletti et al., *Journal of Immunological Methods*, 139(2), 271-279 (1991).
Oda et al., *Biochemical and Biophysical Research Communications*, 193(3), 897-904 (1993).
Ohmichi et al., *The Journal of Biological Chemistry*, 267(21), 14604-14610 (1992).
Ostade et al., *Nature*, 361(6409), 266-269 (1993).
Padlan et al., *Molecular Immunology*, 28(4/5), 489-498 (1991).
Padlan et al., *Molecular Immunology*, 31(3), 169-217 (1994).
Patel et al., *Molecular Carcinogenesis*, 18(1), 1-6 (1997).
Patel et al., *Oral Oncology*, 33(3), 197-203 (1997).
Patel et al., *Molecular Medicine*, 3(10), 674-685 (1997).
Patel et al., *ACTA Oncological*, 37(5), 475-478 (1998).
Pfeifer et al., *Proceedings of the National Academy of Sciences of the United States of America*, 86(24), 10075-10079 (1989).
Pfeifer et al., *Biochemical and Biophysical Research Communications*, 252(1), 481-486 (1998).
Philip, *Molecular and Cellular Biology*, 14(4), 2411-2418 (1994).
Pinckard et al., *Clinical and Experimental Immunology*, 2, 331-340 (1967).
Prasad et al., *Molecular and Cellular Biology*, 12(11), 5260-5267 (1992).
Pulverer et al., *Nature*, 353(6345), 670 (1991).
Qureshi et al., *The Journal of Biological Chemistry*, 266(31), 20594-20597 (1991).
Ram et al., *Cancer Research*, 53(1), 83-88 (1993).
Rapp et al., *The Oncogene Handbook*, (Elsevier Science Publishers, New York), 213-253 (1988).
Rapp, *Oncogene*, 6(4), 495-500 (1991).
Rebay et al., *Cell*, 67, 687-699 (1991).
Rees et al., *The EMBO Journal*, 7(7), 2053-2061 (1988).
Riedel et al., *European Journal of Immunology*, 12, 3146-3150 (1993).
Robbins et al., *Diabetes*, 36(7), 838-845 (1987).
Rogers et al., *Genomics*, 39(2), 127-135 (1997).
Roggenkamp et al., *Molecular & General Genetics*, 202(2), 302-308 (1986).
Rosenfeld et al., *Science*, 252(5004), 431-434 (1991).
Sacchi et al., *Archives of Otolaryngology-Head & Neck Surgery*, 117(3), 321-326 (1991).
Samuels et al., *Molecular and Cellular Biology*, 13(10), 6241-6252 (1993).
Samulski et al., *Journal of Virology*, 63(9), 3822-3828 (1989).
Sarubbi et al., *Analytical Biochemistry*, 237(1), 70-75 (1996).
Sata et al., *The Journal of Biological Chemistry*, 273(50), 331033-33106 (1998).
Schaap et al., *The Journal of Biological Chemistry*, 268(27), 20232-20236 (1993).
Schneider et al., *Tetrahedron Letters*, 31(3), 335-338 (1990).
Seth et al., *The Journal of Biological Chemistry*, 266(35), 23521 (1991).
Siebenlist et al., *Cell*20(1), 269 (1980).
Siegel et al., *The Journal of Immunology*151(8), 4116-4127 (1993).
Smith et al., *Proceedings of the National Academy of Sciences of the United States of America*, 82(24), 8404-8408 (1985).
Smith et al., *Journal of Molecular Biology*, 224(4), 899-904 (1992).
Smith et al., *Advances in Applied Mathematics*, 2(4), 482-489 (1981).
Soldatenkov et al., *The Cancer Journal from Scientific American*, 3(1), 13-20 (1997).
Sozeri et al., *Oncogene*, 7(11), 2259 (1992).
Srinivasula et al., *The Journal of Biological Chemistry*, 272(30), 18542-18545 (1997).
Stanton et al., *Molecular and Cellular Biology*, 9(2), 639-647 (1989).
Stein, *Biochimica et Biophysica Acta*, 1489(1), 45-52 (1999).
Stenflo, *Blood*, 78(7). 1637-1651 (1991).
Stokoe et al., *The EMBO Journal*, 11(11), 3985-3994 (1992).
Sturgill et al., *Nature*, 334(6184), 715-718 (1988).
Sun et al., *Hepatology*, 27(1), 228-239 (1998).
Sunnerhagen et al., *The Journal of Biological Chemistry*, 268(31), 2339-2344 (1993).
Suy et al., *Oncogene*, 15(1), 53-61 (1997).
Suy et al., *The Journal of Biological Chemistry*, 273(28), 1787117878 (1998).
Takamiya et al., *Journal of Neuroscience Research*, 33(3), 493-503 (1992).
Tewari et al., *The Journal of Biological Chemistry*, 270(39), 22705-22708 (1995).
Thome et al., *Nature*, 386(6624), 517-521 (1997).
Tilburn et al., *Gene*, 26(2&3), 205-221 (1983).
Tornkvist et al., *The Journal of Biological Chemistry*, 269(19), 13919-13921 (1994).
Traverse et al., *Oncogene*, 8(11), 3175-3181 (1993).
Troppmair et al., *Mechanisms in B-Cell Neoplasia 1992*, 453-460 (1992).
Turner et al., *Proceedings of the National Academy of Sciences of the United States of America*, 90(12), 5544-5548 (1993).
Uhlmann et al., *Chemical Reviews*, 90(4), 543-584 (1990).
Van Den Berg et al., *Bio/Technology*, 8(2), 135139 (1990).
Verhoeyer et al., *Science*, 239(4847), 1534-1536 (1988).
Vile et al., *Cancer Research.*, 53(5), 962-967 (1993).
Vile et al., *Cancer Research*, 53(17), 3860-3864 (1993).
Vincent et al., *Nature Genetics*, 5, 130-134 (1993).
Vlak et al., *The Journal of General Virology*, 69(4) 765-776 (1988).
Wang et al., *Cell*, 87(4), 629-638 (1996).
Warne et al., *Nature*, 364(6435), 352-355 (1993).
Weiss et al., *Journal of the National Cancer Institute*, 23, 51-54 (1998).
Welling et al., *FEBS Letters*, 188(2), 215-218 (1985).
Winitz et al., *The Journal of Biological Chemistry*, 268(26), 19196-19199 (1993).
Woffendin, *Proceedings of the National Academy of Sciences of the United Satates of America*, 91(24), 11581-11585 (1994).
Wotten et al., *The Journal of Biological Chemistry*, 268(24), 17975-17982 (1993).
Wu, *The Journal of Biological Chemistry*, 264(29), 16985-16987 (1989).
Yeh et al., *The Journal of Experimental Medicine*, 188(10), 1795-1802 (1998).
Yelton et al., *Proceedings of the National Academy of Sciences of the United States of America*, 81(5), 1470-1474 (1984).
Zabner et al., *Cell*, 75(2), 207-216 (1993).
Zhang et al., *Nature*, 364(6435), 308-313 (1993).
Gabra et al., "Definition and refinement of a region of loss of heterozygosity at 11q23.3-q24.3 in epithelial ovarian cancer associated with poor prognosis," PubMed ID 8640783 (Abstract) (*Cancer Res.*, 56 (5), 950-954 (Mar. 1, 1996)).
Gentile et al., "Frequent allelic losses at 11q24.1-q25 in young women with breast cancer: association with poor survival," *Br. J. Cancer*, 80 (5/6), 843-849 (1999).
Hattori et al., "Homo sapiens 247,976 genomic DNA of 11q23," Database NCBI Nucleotide, Acc. No. AP001359 (Aug. 19, 2000).
International Search Report in PCT/US02/10848 (Dec. 12, 2005).
Launonen et al., "Chromosome 11q22.3-q25 LOH in ovarian cancer: association with a more aggressive disease course and involved subregions," Database SciSearch on STN, Accession. No. 1998:941058 (*Gynecol. Oncol.*, 71 (2), 299-304 (Nov. 1998)).
Wang et al., "Single amino acid substitution in constant Region 1 or 4 of gp120 causes the phenotype of a Human Immunodeficiency Virus Type 1 Variant with mutations in hypervariable Region 1 and 2 to revert," *J. Virol.*, 70 (1), 607-611 (Jan. 1996).

\* cited by examiner cDNA SEQUENCE OF BRCC2.

| | | | | |
|---|---|---|---|---|
| ATGATGTTGT | GTTTGGAGAA | AAGAGAGAAG | AGAATTGAAT | AAGTACATGA 50 |
| CCCCTTGGAA | GCTGTTTTCA | GTTGAGGATT | TTGGTGAGTA | GCCACTTGAA 100 |
| ATCAAGGGAA | ATTCCATGAA | TAGCAGGAGC | TGGGAAGAAA | GGAAGAGGAG 150 |
| GAAGGATCCC | ACCACTTTTT | TCTTCCCATC | TAACACCGTG | CTTATGCAAA 200 |
| GCATAGTCCA | TATGAGATCT | GCCTTATAAA | AACTTGCTGA | ATAAAGCGAA 250 |
| TGGAAGTTAA | ATTTTGGACT | TTCTTCCATA | ATAGCTTCAA | ATTATGGTGA 300 |
| CTTGTTGCC | TATAGGGGC | CAGGAAGTAC | ATTTCTTTGA | GATCCTAGAA 350 |
| TCTGAGTGTG | TGCTGTACAC | AGGATGGATA | GAGCCGAGCCT | CTGGCCAGTTG 400 |
| CATTTATCCA | GAGCGAAAAG | CACGCCTGCG | AGTGGAGGCG | CTCTTCGGTT 450 |
| GCAAGCAAGA | ACCTATGTTG | CTAAGGAAA | CAGTGCTTTC | TCTTAAAAGG 500 |
| TACAATCTTG | GCTCCTGTGCC | CATGAAGCGG | AATGTTCGTG | GACATGTGCT 550 |
| TCAGAGACCT | TCCTATTTAA | CCAGGATAGA | AGTTACATTG | TTATGCAATT 600 |
| CCTCTGCTGA | GGGCCTGTAA | AAGGAGTGAG | TTAGGACAGA | TGCAGCAAGA 650 |
| TATTAGGACA | GATTCGCCC | ATTATTCAGG | CTGCACAACA | CAGAAGGAAA 700 |
| CTTGATTTCA | ATAAGACCCA | ATCTTAACA | GTCTTTTCTA | CCCACTTTTA 750 |
| CCCATAACTT | TTCCAAATTT | GGTTCAAATT | GTGCAGAGAA | ACAATAAAAT 800 |
| TTTAAAAAG | GATAAACTGG | CTAGTTAAAA | GTAAATGGCA | TTTAATTAAA 850 |
| ACAAATCTTG | CA | | | |

FIG. 1 cDNA AND PREDICTED AMINO ACID SEQUENCES OF BRCC2

```
294  ATG GTG ACT TTG TTG CCT ATA GAG GGC CAG GAA GTA CAT TTC TTT
      M   V   T   L   L   P   I   E   G   Q   E   V   H   F   F

339  GAG ATC CTA GAA TCT GAG TGT GTG CTC TAC ACA GGA TGG ATA GAG
      E   I   L   E   S   E   C   V   L   Y   T   G   W   I   E

384  CGA GCC TCT GGC AGT TCC ATT TAT CCA GAG GCA AAA GCA CGC CTG
      R   A   S   G   S   S   I   Y   P   E   A   K   A   R   L

429  CCA CTG GAG GCG CTC TTG GGT TCC AAC AAA GAA CCT ATG TTG CCT
      P   L   E   A   L   L   G   S   N   K   E   P   M   L   P

474  AAG GAA ACA GTG CTT TCT CTT AAA AGG TAC AAT CTT GGC TCC TCT
      K   E   T   V   L   S   L   K   R   Y   N   L   G   S   S

519  GCC ATG AAG CGG AAT GTT CCT GGA CAT GTG CTT CAG AGA CCT TCC
      A   M   K   R   N   V   P   G   H   V   L   Q   R   P   S

564  TAT TTA ACC AGG ATA CAA GTT ACA TTG TTA TGC AAT TCC TCT GCT
      Y   L   T   R   I   Q   V   T   L   L   C   N   S   S   A

609  GAG GCC CTG TAA
      E   A   L   *
```

*FIG. 2*

SEQUENCE LISTING

```
<160> NUMBER OF SEQ ID NOS: 2

<210> SEQ ID NO 1
<211> LENGTH: 862
<212> TYPE: DNA
<213> ORGANISM: Homo sapiens
<220> FEATURE:
<221> NAME/KEY: CDS
<222> LOCATION: (294)..(620)

<400> SEQUENCE: 1
atgatgttgt gtttggagaa aagagagaag agaattgaat aagtacatga ccccttggaa     60
gctgttttca gttgaggatt ttggtgagta gccacttgaa atcaagggaa attccatgaa    120
tagcaggagc tgggaagaaa ggaagaggag gaaggatccc accacttttt tcttcccatc    180
taacaccgtg cttatgcaaa gcatagtcca tatgagatct gccttataaa aacttgctga    240
ataaagcgaa tggaagttaa attttggact ttcttccata atagcttcaa att atg       296
                                                             Met
                                                             1 gtg act ttg ttg cct ata gag ggc cag gaa gta cat ttc ttt gag atc      344
Val Thr Leu Leu Pro Ile Glu Gly Gln Glu Val His Phe Phe Glu Ile
```

```
              5                   10                  15
cta gaa tct gag tgt gtg ctc tac aca gga tgg ata gag cga gcc tct    392
Leu Glu Ser Glu Cys Val Leu Tyr Thr Gly Trp Ile Glu Arg Ala Ser
             20                  25                  30 ggc agt tcc att tat cca gag gca aaa gca cgc ctg cca ctg gag gcg    440
Gly Ser Ser Ile Tyr Pro Glu Ala Lys Ala Arg Leu Pro Leu Glu Ala
         35                  40                  45 ctc ttg ggt tcc aac aaa gaa cct atg ttg cct aag gaa aca gtg ctt    488
Leu Leu Gly Ser Asn Lys Glu Pro Met Leu Pro Lys Glu Thr Val Leu
 50                  55                  60                  65 tct ctt aaa agg tac aat ctt ggc tcc tct gcc atg aag cgg aat gtt    536
Ser Leu Lys Arg Tyr Asn Leu Gly Ser Ser Ala Met Lys Arg Asn Val
                 70                  75                  80 cct gga cat gtg ctt cag aga cct tcc tat tta acc agg ata caa gtt    584
Pro Gly His Val Leu Gln Arg Pro Ser Tyr Leu Thr Arg Ile Gln Val
             85                  90                  95 aca ttg tta tgc aat tcc tct gct gag gcc ctg taa aaggagtgag         630
Thr Leu Leu Cys Asn Ser Ser Ala Glu Ala Leu
            100                 105 ttaggacaga tgcagcaaga tattaggaca gatttcgccc attattcagg ctgcacaaca    690
cagaaggaaa cttgatttca ataagaccca attcttaaca gtcttttcta cccactttta    750
cccataactt ttccaaattt ggttcaaatt gtgcagagaa acaataaaat ttttaaaaag    810
gataaactgg ctagttaaaa gtaaatggca tttaattaaa acaaatcttg ca            862

<210> SEQ ID NO 2
<211> LENGTH: 108
<212> TYPE: PRT
<213> ORGANISM: Homo sapiens
<220> FEATURE:
<223> OTHER INFORMATION: cDNA

<400> SEQUENCE: 2

Met Val Thr Leu Leu Pro Ile Glu Gly Gln Glu Val His Phe Phe Glu
 1               5                  10                  15

Ile Leu Glu Ser Glu Cys Val Leu Tyr Thr Gly Trp Ile Glu Arg Ala
             20                  25                  30

Ser Gly Ser Ser Ile Tyr Pro Glu Ala Lys Ala Arg Leu Pro Leu Glu
         35                  40                  45

Ala Leu Leu Gly Ser Asn Lys Glu Pro Met Leu Pro Lys Glu Thr Val
     50                  55                  60

Leu Ser Leu Lys Arg Tyr Asn Leu Gly Ser Ser Ala Met Lys Arg Asn
 65                  70                  75                  80

Val Pro Gly His Val Leu Gln Arg Pro Ser Tyr Leu Thr Arg Ile Gln
                 85                  90                  95

Val Thr Leu Leu Cys Asn Ser Ser Ala Glu Ala Leu
            100                 105
```

GENE BRCC-2 AND DIAGNOSTIC AND THERAPEUTIC USES THEREOF

CROSS REFERENCE TO RELATED APPLICATIONS

This application is a continuation of copending International Patent Application PCT/US02/10848, which was filed on Apr. 8, 2002, which designates the United States of America, which was published under the Patent Cooperation Treaty on Oct. 17, 2002 as Publication Number WO 02/081639, and which (as filed and as published) is incorporated by reference in its entirety herein. This application also claims benefit of priority to Provisional Application Ser. No. 60/281,796, filed Apr. 6, 2001, which is incorporated by reference in its entirety herein.

STATEMENT REGARDING FEDERALLY SPONSORED RESEARCH AND DEVELOPMENT

This invention was made with government support under grant numbers CA58984, CA68322, and CA74175 awarded by NIH. The Government has certain rights in the invention.

FIELD OF THE INVENTION

The present invention relates to a gene that encodes a polypeptide that modulates apoptosis. This polypeptide is a useful target for identifying compounds that inhibit cancer progression by modulating apoptosis. Also, this polypeptide is useful as a diagnostic target for detecting cancers wherein this polypeptide is overexpressed, e.g., breast cancer and lung cancer.

BACKGROUND OF THE INVENTION

Alterations in the cellular genes which directly or indirectly control cell growth and differentiation are considered to be the main cause of cancer. The raf gene family includes three highly conserved genes termed A-, B- and c-raf (also called raf-1). Raf genes encode protein kinases that are thought to play important regulatory roles in signal transduction processes that regulate cell proliferation. Expression of the c-raf protein is believed to play a role in abnormal cell proliferation since it has been reported that 60% of all lung carcinoma cell lines express unusually high levels of c-raf mRNA and protein. Rapp et al., The Oncogene Handbook, E. P. Reddy, A. M Skalka and T. Curran, eds., Elsevier Science Publishers, New York, 1988, pp. 213-253.

Malignant tumors develop through a series of stepwise, progressive changes that lead to the loss of growth control characteristic of cancer cells, i.e., continuous unregulated proliferation, the ability to invade surrounding tissues, and the ability to metastasize to different organ sites. Carefully controlled in vitro studies have helped define the factors that characterize the growth of normal and neoplastic cells and have led to the identification of specific proteins that control cell growth and differentiation.

As discussed above, the raf genes are members of a gene family which encode related proteins termed A-, B- and c-raf. Raf genes code for highly conserved serine-threonine-specific protein kinases. These enzymes are differentially expressed; c-raf, the most thoroughly characterized, is expressed in all organs and in all cell lines that have been examined. A- and B-raf are expressed in urogenital and brain tissues, respectively. c-raf protein kinase activity and subcellular distribution are regulated by mitogens via phosphorylation. Various growth factors, including epidermal growth factor, acidic fibroblast growth factor, platelet-derived growth factor, insulin, granulocyte-macrophage colony-stimulating factor, interleukin-2, interleukin-3 and erythropoietin, have been shown to induce phosphorylation of c-raf. Thus, c-raf is believed to play a fundamental role in the normal cellular signal transduction pathway, coupling a multitude of growth factors to their net effect, cellular proliferation.

Certain abnormal proliferative conditions are believed to be associated with raf expression and are, therefore, believed to be responsive to inhibition of raf expression. Abnormally high levels of expression of the raf protein are also implicated in transformation and abnormal cell proliferation. These abnormal proliferative conditions are also believed to be responsive to inhibition of raf expression. Examples of abnormal proliferative conditions are hyperproliferative disorders such as cancers, tumors, hyperplasias, pulmonary fibrosis, angiogenesis, psoriasis, atherosclerosis and smooth muscle cell proliferation in the blood vessels, such as stenosis or restenosis following angioplasty. The cellular signaling pathway of which raf is a part has also been implicated in inflammatory disorders characterized by T-cell proliferation (T-cell activation and growth), such as tissue graft rejection, endotoxin shock, and glomerular nephritis, for example.

Oligonucleotides have been employed as therapeutic moieties in the treatment of disease states in animals and man. For example, workers in the field have now identified antisense, triplex and other oligonucleotide compositions which are capable of modulating expression of genes implicated in viral, fungal and metabolic diseases. Antisense oligonucleotide inhibition of gene expression has proven to be a useful tool in understanding the roles of raf genes. An antisense oligonucleotide complementary to the first six codons of human c-raf has been used to demonstrate that the mitogenic response of T cells to interleukin-2 (IL-2) requires c-raf. Cells treated with the oligonucleotide showed a near-total loss of c-raf protein and a substantial reduction in proliferative response to IL-2. Riedel et al., Eur. J. Immunol. 1993, 23, 3146-3150. Rapp et al. have disclosed expression vectors containing a raf gene in an antisense orientation downstream of a promoter, and methods of inhibiting raf expression by expressing an antisense Raf gene or a mutated Raf gene in a cell. WO application 93/04170. An antisense oligodeoxyribonucleotide complementary to codons 1-6 of murine c-Raf has been used to abolish insulin stimulation of DNA synthesis in the rat hepatoma cell line H4IIE. Tornkvist et al., J. Biol. Chem. 1994, 269, 13919-13921. WO Application 93/06248 discloses methods for identifying an individual at increased risk of developing cancer and for determining a prognosis and proper treatment of patients afflicted with cancer comprising amplifying a region of the c-raf gene and analyzing it for evidence of mutation. Denner et al. discloses antisense polynucleotides hybridizing to the gene for raf, and processes using them. WO 94/15645. Oligonucleotides hybridizing to human and rat raf sequences are disclosed. Iversen et al. discloses heterotypic antisense oligonucleotides complementary to raf which are able to kill ras-activated cancer cells, and methods of killing raf-activated cancer cells. Numerous oligonucleotide sequences are disclosed, none of which are actually antisense oligonucleotide sequences.

U.S. Pat. No. 5,919,773, to Monia et al. discloses that elimination or reduction of raf gene expression can halt or reverse abnormal cell proliferation. The Monia et al. patent discloses Oligonucleotides targeted to nucleic acids encoding raf. This relationship between an oligonucleotide and its complementary nucleic acid target to which it hybridizes is commonly referred to as "antisense."

It is noted however, that raf-1 involvement marks only a component in a complex growth and cell survival/death pathway, the identification of other components of which may allow more selective, more specific and/or more efficacious targeting of such components. Identification of one or more genes associated with such components would highly beneficial.

OBJECTS AND SUMMARY OF THE INVENTION

It is an object of the invention to provide a novel gene that encodes a polypeptide which is a component of cell survival/death pathway which is other than the raf-1 component.

It is a more specific object of the invention to provide a BRCC2 nucleic acid sequence identified in FIG. 1 having SEQ ID NO:1.

It is another specific object of the invention to provide a BRCC2 nucleic acid sequence encoding the polypeptide identified in FIG. 2 (ORF) and having SEQ ID NO:2, or a homolog or analog thereof, that encodes a polypeptide having at least 90% sequence identity to said polypeptide, or a fragment thereof that encodes a polypeptide that mediates apoptosis.

It is another specific object of the invention to provide a nucleic acid sequence corresponding to nucleotides 294 to 620 of SEQ ID NO:1 contained in FIG. 1 or a fragment thereof which is at least 100 nucleotides in length.

It is another object of the invention to provide a BRCC2 polypeptide that mediates apoptosis comprising the amino acid sequence contained in SEQ ID NO:2, which sequence is depicted in FIG. 2, or a fragment thereof which is at least 50 amino acids in length or an analog or homolog having at least 90% sequence identity to said polypeptide which mediates apoptosis.

It is another object of the invention to provide an antibody that specifically binds BRCC2 polypeptide.

It is another specific object of the invention to provide a method for identifying compounds that modulate apoptosis by screening for compounds that specifically bind BRCC2 polypeptide.

It is another specific object of the invention to provide a method for detecting or evaluating the prognosis of a cancer characterized by overexpression of BRCC2 by detecting expression of BRCC2 in an analyte obtained from a patient tested for cancer and correlating the level of expression to a positive or negative diagnosis for cancer.

It is another object to provide a method of treating or preventing a cancer characterized by overexpression of BRCC2 comprising administering a compound that modulates BRCC2 gene expression and/or activity of BRCC2 polypeptide.

It is yet another object to provide a method for treating cancer comprising administering at least one antisense oligonucleotide or ribozyme that inhibits BRCC2 expression, thereby inhibiting cancer cell proliferation and/or metastatic potential.

It is still another object of the invention to provide a pharmaceutical composition for the treatment of cancer that comprises an antagonist of BRCC2 expression and/or activity and a pharmaceutically acceptable carrier. Preferably, such compositions will comprise liposomal formulations.

Another object of the invention is to provide diagnostic compositions for detection of cancer that comprise an oligonucleotide that specifically binds BRCC2 DNA or an antibody that specifically binds the BRCC2 polypeptide, attached directly or indirectly to a label, and a diagnostically acceptable carrier.

It is another object of the invention to provide methods for inhibiting tumor growth and/or metastasis by administration of a molecule that antagonizes the expression and/or activity of BRCC2.

It is a preferred object of the invention to provide liposomal formulations for antisense therapy that inhibit tumor growth and/or metastasis which comprise antisense oligonucleotides specific to BRCC2, optionally in association with cytotoxic moieties such as radionuclides.

DETAILED DESCRIPTION OF THE FIGURES

FIG. 1. cDNA sequence of BRCC2, SEQ ID NO:1. The figure shows SEQ ID NO:1, the nucleotide sequence of a BRCC2 cDNA clone (862 bp), isolated from human breast cancer cells (MDA-MB 231) by the differential display of mRNA approach (GenBank Accession nos. AF220061 and AF303179). Nucleotide positions are indicated by numbers on the right. Shaded area represents the coding region (294-620 bp). Based on the genomic database search, BRCC2 is an intronless gene located on chromosome 11q (GenBank accession no. AP001359, clone RP11-820L6).

FIG. 2. cDNA, SEQ ID NO:1, and predicted amino acid sequences of BRCC2, SEQ ID NO:2. The figure shows the nucleotide positions are indicated by numbers on the left. The predicted longest open reading frame (ORF) (108 amino acids) is shown. Motifs and other signature sequences were detected by domain database search (PROSITE). Underlined amino acids, N- glycosylation site; shaded residues, Protein Kinase C phosphorylation site; bolded residues, Casein Kinase II phosphorylation site. The nuclear localization of BRCC2 protein was predicted by Reinhardt's method.

FIG. 3. Normal tissue distribution of BRCC2 gene expression. Human adult tissue mRNA blots (Clontech) were probed with $^{32}$P-labeled BRCC2 cDNA fragment. The blots were reprobed with β-Actin cDNA. As shown, BRCC mRNA (~1.2 kb) is expressed in most normal tissues.

Figure 4:
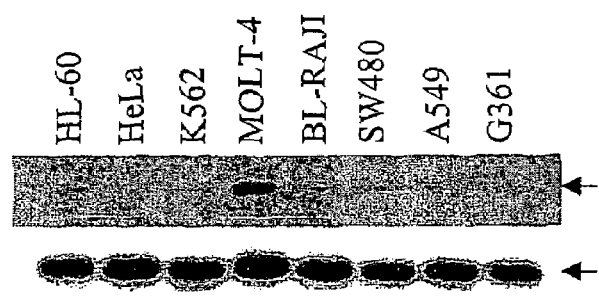

FIG. 4. Expression of BRCC2 transcript in human cancer cell lines. Cancer cell line blot (Clontech) was probed with $^{32}$P-labeled BRCC2 cDNA fragment. The blots were reprobed with β-Actin cDNA. HL-60, promyelocytic leukemia; K562, chronic myelogenous leukemia;. MOLT4, lymphoblastic leukemia; BL-RAJI, Burkitt's lymphoma; SW480, colorectal adenocarcinoma; A549, lung carcinoma; G361, melanoma.

Figure 5:
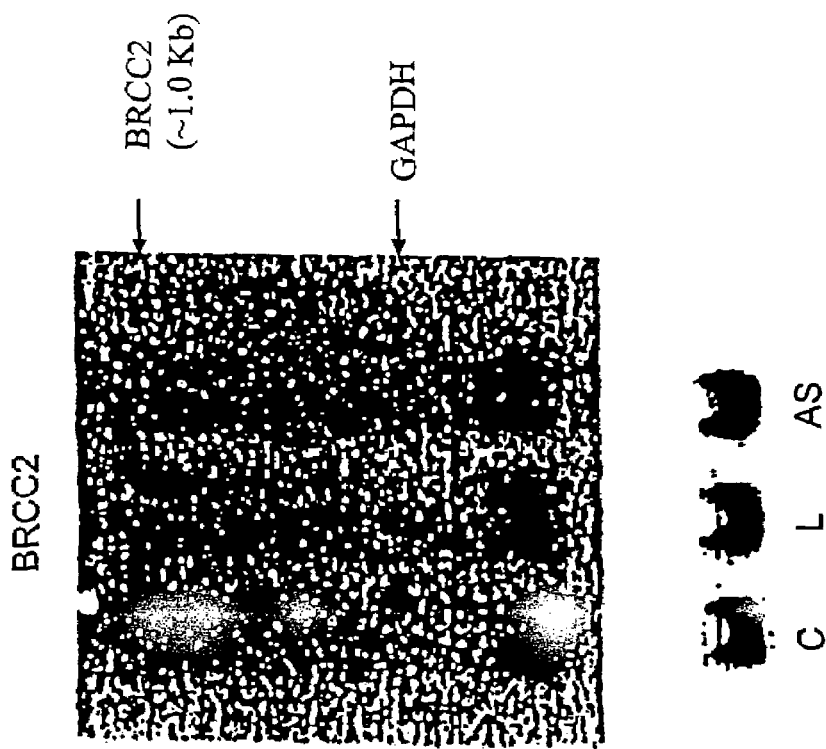

FIG. 5. This figure shows the decrease in BRCC2 gene expression in breast cancer cells (BRCC) treated with antisense raf oligonucleotide (AS-raf_ODN).

DETAILED DESCRIPTION OF THE INVENTION

The molecular genetic factors that negate cell death and contribute to tumor growth and metastasis can be attractive targets for therapeutic intervention. In a search for such genes, the present inventors have identified a full-length cDNA encoding a gene which is hereby named as BRCC2 that is a modulator of apoptosis.

The expression of the gene BRCC-2 (FIG. 1 SEQ ID NO:1) is decreased in human breast cancer cells (BRCC) treated with a novel antisense raf oligonucleotide (AS-raf- ODN) (FIG. 5). AS-raf-ODN causes programmed cell death in cancer cells by decreasing the amount of a proliferation and survival—promoting protein Raf-1. Thus, the present inventors have shown that BRCC-2 is a component of growth and cell survival/death pathway in cancer cells and is regulated by Raf-1 protein. In linking the expression of BRCC2 to the modulation of Raf-1, the present inventors have shown that BRCC2 is up regulated by Raf-1 and therefore this newly discovered gene is a component of the cell survival/cell death pathway. More particularly, the present invention is based, at least in part, on the discovery that the BRCC2 gene plays a role down stream of raf-1.

Other aspects of the present invention are based on the discovery that the manipulation of the level of BRCC-2 in cancer cells provides therapeutic advantages. For example, decreasing the amount of BRCC-2 induces many of the in vivo effects of antisense raf oligonucleotide such as tumor growth arrest, tumor regression, tumor cell death and/or potentiate radiation/drug-induced cytotoxicity. In addition, being a target potentially downstream of Raf-1, it is anticipated that greater specificity is obtained by targeting the action of BRCC2 as compared with Raf-1.

In identifying the role played BRCC2 the inventors have examined changes in gene expression profiles in breast cancer cells treated with antisense raf oligodeoxyribonucleotide (ODN). (FIG. 5) Treatment of MDA-MB 231 breast cancer cells with antisense raf ODN (ISIS 5132, 2 µM, 48 h) in the presence of lipofectin led to significant inhibition of Raf-1 protein (62%) as compared to control lipofectin-treated or untreated cells. Raf-1 inhibition was associated with apoptosis as indicated by a 8-fold increase in a caspase-3 like protease activity. PARP cleavage, and a 5-fold increase in the sub-G1 population was observed in antisense raf ODN-treated cells. We used the differential display of mRNA strategy to identify changes in gene expression as a result of antisense raf ODN-treatment of MDA-MB 231 cells. The partial cDNA fragment of novel gene, BRCC2 (862 bp) was subcloned. Northern blot analysis revealed BRCC2 transcripts of □1.2 kb, in normal human tissues and cancer cell lines. The BRCC2 cDNA sequence revealed a putative ORF of 108 amino acids. Antisense raf ODN treatment of MDA-MB 231 cells caused inhibition of the steady state mRNA levels of BRCC2 by 42.2%.

Based on these discoveries, the present invention relates to a novel gene, BRCC2, that modulates apoptosis, the corresponding polypeptide, and application thereof in diagnostic and therapeutic methods. Particularly, the invention provides a novel target for identifying compounds that promote apoptosis of cancer cells, especially breast and lung cancer.

As noted, the invention is broadly directed to a novel gene referred to as BRCC2. Reference to BRCC2 herein is intended to be construed to include BRCC2 proteins of any origin which are substantially homologous to and which are biologically equivalent to the BRCC2 characterized and described herein. Such substantially homologous BRCC2s may be native to any tissue or species and, similarly, biological activity can be characterized in any of a number of biological assay systems.

The term "biologically equivalent" is intended to mean that the compositions of the present invention are capable of demonstrating some or all of the same biological properties in a similar fashion, not necessarily to the same degree as the BRCC2 isolated as described herein or recombinantly produced human BRCC2 of the invention.

By "substantially homologous" it is meant that the degree of homology of human BRCC2 from any species is greater than that between BRCC2 and any previously reported apoptopic modulating gene.

Sequence identity or percent identity is intended to mean the percentage of same residues between two sequences, wherein the two sequences are aligned using the Clustal method (Higgins et al, Cabios 8:189-191, 1992) of multiple sequence alignment in the Lasergene biocomputing software (DNASTAR, INC, Madison, Wis.). In this method, multiple alignments are carried out in a progressive manner, in which larger and larger alignment groups are assembled using similarity scores calculated from a series of pairwise alignments. Optimal sequence alignments, determined from a residue weight table representing the probability of a given amino acid change occurring in two related proteins over a given evolutionary interval. Penalties for opening the lengthening gaps in the alignment contribute to the score. The default parameters used with this program are as follows: gap penalty for multiple alignment=IO; gap length penalty for multiple alignment=10; k-tuple value in pairwise alignment=1; gap penalty in pairwise alignment=3; window value in pairwise alignment=5; diagonals saved in pairwise alignmentz=5. The residue weight table used for the alignment program is PAM250 (Dayhoff et al., in Atlas of Protein Sequence and Structure, Dayhoff, Ed., NDRF, Washington, Vol. 5, suppl. 3, p. 345, 1978).

Percent conservation is calculated from the above alignment by adding the percentage of identical residues to the percentage of positions at which the two residues represent a conservative substitution (defined as having a log odds value of greater than or equal to 0.3 in the PAM250 residue weight table). Conservation is referenced to human BRCC2 when determining percent conservation with non-human BRCC2, and referenced to BRCC2 when determining percent conservation with non- BRCC2 proteins. Conservative amino acid changes satisfying this requirement are: R-K; E-D, Y-F, L-M; V-I, Q-H.

Polypeptide Fragments

The invention provides polypeptide fragments of the disclosed proteins. Polypeptide fragments of the invention can comprise at least 8, 10, 12, 15, 18, 19, 20, 25, 50, 75, 100, or 108 contiguous amino acids of the amino acid sequence contained in FIG. 2 (SEQ ID NO:2). Also included are all intermediate length fragments in this range, such as 51, 52, 53, etc.; 70, 71, 72, etc.; and 100, 101, 102, etc., which are exemplary only and not limiting.

Biologically Active Variants

Variants of the BRCC2 polypeptide disclosed herein can also occur. Variants can be naturally or non-naturally occurring. Naturally occurring variants are found in humans or other species and comprise amino acid sequences which are substantially identical to the amino acid sequence shown in FIG. 1 (SEQ ID NO:1). Species homologs of the protein can be obtained using subgenomic polynucleotides of the invention, as described below, to make suitable probes or primers to screening cDNA expression libraries from other species, such as mice, monkeys, yeast, or bacteria, identifying cDNAs which encode homologs of the protein, and expressing the cDNAs as is known in the art.

Non-naturally occurring variants which retain substantially the same biological activities as naturally occurring protein variants are also included here. Preferably, naturally or non-naturally occurring variants have amino acid sequences which are at least 85%, 90%, or 95% identical to the amino acid sequence shown in FIG. 1 (SEQ ID NO:1).

More preferably, the molecules are at least 96%, 97%, 98% or 99% identical. Percent identity is determined using any method known in the art. A non-limiting example is the Smith-Waterman homology search algorithm using an affine gap search with a gap open penalty of 12 and a gap extension penalty of 1. The Smith-Waterman homology search algorithm is taught in Smith and Waterman, *Adv. Appl. Math.* (1981) 2:482-489.

Guidance in determining which amino acid residues can be substituted, inserted, or deleted without abolishing biological or immunological activity can be found using computer programs well known in the art, such as DNASTAR software. Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

A subset of mutants, called muteins, is a group of polypeptides in which neutral amino acids, such as serines, are substituted for cysteine residues which do not participate in disulfide bonds. These mutants may be stable over a broader temperature range than native secreted proteins. See Mark et al., U.S. Pat. No. 4,959,314.

It is reasonable to expect that an isolated replacement of a leucine with an isoleucine or valine, an aspartate with a glutamate, a threonine with a serine, or a similar replacement of an amino acid with a structurally related amino acid will not have a major effect on the biological properties of the resulting secreted protein or polypeptide variant. Properties and functions of BRCC2 or polypeptide variants are of the same type as a protein comprising the amino acid sequence encoded by the nucleotide sequence shown in FIG. 1 (SEQ ID NO:1), although the properties and functions of variants can differ in degree.

BRCC2 protein variants include glycosylated forms, aggregative conjugates with other molecules, and covalent conjugates with unrelated chemical moieties. BRCC2 protein variants also include allelic variants, species variants, and muteins. Truncations or deletions of regions which do not affect the differential expression of the BRCC2 protein gene are also variants. Covalent variants can be prepared by linking functionalities to groups which are found in the amino acid chain or at the N- or C-terminal residue, as is known in the art.

It will be recognized in the art that some amino acid sequence of the BRCC2 protein of the invention can be varied without significant effect on the structure or function of the protein. If such differences in sequence are contemplated, it should be remembered that there are critical areas on the protein which determine activity. In general, it is possible to replace residues that form the tertiary structure, provided that residues performing a similar function are used. In other instances, the type of residue may be completely unimportant if the alteration occurs at a non-critical region of the protein. The replacement of amino acids can also change the selectivity of binding to cell surface receptors. Ostade et al., *Nature* 361:266-268 (1993) describes certain mutations resulting in selective binding of TNF-alpha to only one of the two known types of TNF receptors. Thus, the polypeptides of the present invention may include one or more amino acid substitutions, deletions or additions, either from natural mutations or human manipulation.

The invention further includes variations of the BRCC2 polypeptide which show comparable expression patterns or which include antigenic regions. Such mutants include deletions, insertions, inversions, repeats, and type substitutions. Guidance concerning which amino acid changes are likely to be phenotypically silent can be found in Bowie, J. U., et al., "Deciphering the Message in Protein Sequences: Tolerance to Amino Acid Substitutions," *Science* 247:1306-1310 (1990).

Of particular interest are substitutions of charged amino acids with another charged amino acid and with neutral or negatively charged amino acids. The latter results in proteins with reduced positive charge to improve the characteristics of the disclosed protein. The prevention of aggregation is highly desirable. Aggregation of proteins not only results in a loss of activity but can also be problematic when preparing pharmaceutical formulations, because they can be immunogenic. (Pinckard et al., *Clin. Exp. Immunol.* 2:331-340 (1967); Robbins et al., *Diabetes* 36:838-845 (1987); Cleland et al., *Crit. Rev. Therapeutic Drug Carrier Systems* 10:307-377 (1993)).

Amino acids in the polypeptides of the present invention that are essential for function can be identified by methods known in the art, such as site-directed mutagenesis or alanine-scanning mutagenesis (Cunningham and Wells, *Science* 244:108 1-1085 (1989)). The latter procedure introduces single alanine mutations at every residue in the molecule. The resulting mutant molecules are then tested for biological activity such as binding to a natural or synthetic binding partner. Sites that are critical for ligand-receptor binding can also be determined by structural analysis such as crystallization, nuclear magnetic resonance or photoaffinity labeling (Smith et al., *J. Mol. Biol.* 224:899-904 (1992) and de Vos et al. *Science* 255:306-3 12 (1992)).

As indicated, changes are preferably of a minor nature, such as conservative amino acid substitutions that do not significantly affect the folding or activity of the protein. Of course, the number of amino acid substitutions a skilled artisan would make depends on many factors, including those described above. Generally speaking, the number of substitutions for any given polypeptide will not be more than 50, 40, 30, 25, 20, 15, 10, 5 or 3.

Fusion Proteins

Fusion proteins comprising proteins or polypeptide fragments of BRCC2 can also be constructed. Fusion proteins are useful for generating antibodies against amino acid sequences and for use in various assay systems. For example, fusion proteins can be used to identify proteins which interact with a protein of the invention or which interfere with its biological function. Physical methods, such as protein affinity chromatography, or library-based assays for protein-protein interactions, such as the yeast two-hybrid or phage display systems, can also be used for this purpose. Such methods are well known in the art and can also be used as drug screens. Fusion proteins comprising a signal sequence and/or a transmembrane domain of BRCC2 or a fragment thereof can be used to target other protein domains to cellular locations in which the domains are not normally found, such as bound to a cellular membrane or secreted extracellularly.

A fusion protein comprises two protein segments fused together by means of a peptide bond. Amino acid sequences for use in fusion proteins of the invention can utilize the amino acid sequence shown in FIG. 2 (SEQ ID NO:2) or can be prepared from biologically active variants of SEQ ID NO:2, such as those described above. The first protein segment can consist of a full-length BRCC2.

Other first protein segments can consist of at least 8, 10, 12, 15, 18, 19, 20, 25, 50, 75, 100, 108 contiguous amino acids selected from SEQ ID NO 2. The contiguous amino acids listed herein are not limiting and also include all intermediate lengths such as 20, 21, 22, etc.; 70, 71, 72, etc.

The second protein segment can be a full-length protein or a polypeptide fragment. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags can be used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain. (DBD) fusions, GAL4 DNA binding domain fusions, and herpes simplex virus (HSV) BP 16 protein fusions.

These fusions can be made, for example, by covalently linking two protein segments or by standard procedures in the art of molecular biology. Recombinant DNA methods can be used to prepare fusion proteins, for example, by making a DNA construct which comprises a coding sequence contained in FIG. 1 (SEQ ID NO:2) in proper reading frame with a nucleotide encoding the second protein segment and expressing the DNA construct in a host cell, as is known in the art. Many kits for constructing fusion proteins are available from companies that supply research labs with tools for experiments, including, for example, Promega Corporation (Madison, Wis.), Stratagene (La Jolla, Calif.), Clontech (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Proteins, fusion proteins, or polypeptides of the invention can be produced by recombinant DNA methods. For production of recombinant proteins, fusion proteins, or polypeptides, a coding sequence of the nucleotide sequence shown in FIG. 1 (SEQ ID NO:1) can be expressed in prokaryotic or eukaryotic host cells using expression systems known in the art. These expression systems include bacterial, yeast, insect, and mammalian cells.

The resulting expressed protein can then be purified from the culture medium or from extracts of the cultured cells using purification procedures known in the art. For example, for proteins fully secreted into the culture medium, cell-free medium can be diluted with sodium acetate and contacted with a cation exchange resin, followed by hydrophobic interaction chromatography. Using this method, the desired protein or polypeptide is typically greater than 95% pure. Further purification can be undertaken, using, for example, any of the techniques listed above.

It may be necessary to modify a protein produced in yeast or bacteria, for example by phosphorylation or glycosylation of the appropriate sites, in order to obtain a functional protein. Such covalent attachments can be made using known chemical or enzymatic methods.

BRCC2 protein or polypeptide of the invention can also be expressed in cultured host cells in a form which will facilitate purification. For example, a protein or polypeptide can be expressed as a fusion protein comprising, for example, maltose binding protein, glutathione-S-transferase, or thioredoxin, and purified using a commercially available kit. Kits for expression and purification of such fusion proteins are available from companies such as New England BioLabs, Pharmacia, and Invitrogen. Proteins, fusion proteins, or polypeptides can also be tagged with an epitope, such as a "Flag" epitope (Kodak), and purified using an antibody which specifically binds to that epitope.

The coding sequence disclosed herein can also be used to construct transgenic animals, such as cows, goats, pigs, or sheep. Female transgenic animals can then produce proteins, polypeptides, or fusion proteins of the invention in their milk. Methods for constructing such animals are known and widely used in the art.

Alternatively, synthetic chemical methods, such as solid phase peptide synthesis, can be used to synthesize a secreted protein or polypeptide. General means for the production of peptides, analogs or derivatives are outlined in Chemistry and Biochemistry of Amino Acids, Peptides, and Proteins—A Survey of Recent Developments, B. Weinstein, ed. (1983). Substitution of D-amino acids for the normal L-stereoisomer can be carried out to increase the half-life of the molecule.

Typically, homologous polynucleotide sequences can be confirmed by hybridization under stringent conditions, as is known in the art. For example, using the following wash conditions: 2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each, homologous sequences can be identified which contain at most about 25-30% basepair mismatches. More preferably, homologous nucleic acid strands contain 15-25% basepair mismatches, even more preferably 5-15% basepair mismatches.

The invention also provides polynucleotide probes which can be used to detect complementary nucleotide sequences, for example, in hybridization protocols such as Northern or Southern blotting or in situ hybridizations. Polynucleotide probes of the invention comprise at least 12, 13, 14, 15, 16, 17, 18, 19, 20, 30, or 40 or more contiguous nucleotides of the sequence contained in FIG. 1 (SEQ ID NO:1). Polynucleotide probes of the invention can comprise a detectable label, such as a radioisotopic, fluorescent, enzymatic, or chemiluminescent label.

Isolated genes corresponding to the cDNA sequences disclosed herein are also provided. Standard molecular biology methods can be used to isolate the corresponding genes using the cDNA sequences provided herein. These methods include preparation of probes or primers from the nucleotide sequence shown in FIG. 1 (SEQ ID NO:1) for use in identifying or amplifying the genes from mammalian, including human, genomic libraries or other sources of human genomic DNA.

Polynucleotide molecules of the invention can also be used as primers to obtain additional copies of the polynucleotides, using polynucleotide amplification methods. Polynucleotide molecules can be propagated in vectors and cell lines using techniques well known in the art. Polynucleotide molecules can be on linear or circular molecules. They can be on autonomously replicating molecules or on molecules without replication sequences. They can be regulated by their own or by other regulatory sequences, as is known in the art.

Polynucleotide Constructs

Polynucleotide molecules comprising the coding sequences disclosed herein can be used in a polynucleotide construct, such as a DNA or RNA construct. Polynucleotide molecules of the invention can be used, for example, in an expression construct to express all or a portion of a protein, variant, fusion protein, or single-chain antibody in a host cell. An expression construct comprises a promoter which is functional in a chosen host cell. The skilled artisan can readily select an appropriate promoter from the large number of cell type-specific promoters known and used in the art. The expression construct can also contain a transcription terminator which is functional in the host cell. The expression construct comprises a polynucleotide segment which encodes all or a portion of the desired protein. The polynucleotide segment is located downstream from the promoter. Transcription of the polynucleotide segment initiates at the promoter. The expression construct can be linear or circular and can contain sequences, if desired, for autonomous replication.

Host Cells

An expression construct can be introduced into a host cell. The host cell comprising the expression construct can be any suitable prokaryotic or eukaryotic cell. Expression systems in bacteria include those described in Chang et al., *Nature* (1978) 275:615; Goeddel et al., *Nature* (1979) 281: 544; Goeddel et al., *Nucleic Acids Res*. (1980) 8:4057; EP 36,776; U.S. Pat. No. 4,551,433; deBoer et al., *Proc. Natl. Acad Sci. USA* (1983) 80: 21-25; and Siebenlist et al., *Cell* (1980) 20: 269.

Expression systems in yeast include those described in Hinnen et al., *Proc. Natl. Acad. Sci. USA* (1978) 75: 1929; Ito et al., *J Bacteriol*. (1983) 153: 163; Kurtz et al., *Mol. Cell. Biol*. (1986) 6:142; Kunze et al., *J. Basic Microbiol*. (1985) 25: 141; Gleeson et al., *J. Gen. Microbiol*. (1986) 132: 3459, Roggenkamp et al., *Mol. Gen. Genet*. (1986) 202:302); Das et al., J Bacteriol. (1984) 158: 1165; De Louvencourt et al., *J Bacteriol*. (1983) 154: 737, Van den Berg et al., *Bio/Technology* (1990) 8: 135; Kunze et al., *J. Basic Microbiol*. (1985) 25: 141; Cregg et al., *Mol. Cell. Biol*. (1985) 5: 3376; U.S. Pat. No. 4,837,148; U.S. Pat. No. 4,929,555; Beach and Nurse, Nature (1981) 300: 706; Davidow et al., *Curr. Genet*. (1985) 1p: 380; Gaillardin et al., Curr. *Genet*. (1985) 10: 49; Ballance et al., *Biochem. Biophys. Res. Commun*. (1983) 112: 284-289; Tilburn et al., *Gene* (1983) 26: 205-22; Yelton et al., *Proc. Natl. Acad, Sci. USA* (1984) 81: 1470-1474; Kelly and Hynes, *EMBO J*. (1985) 4: 475479; EP 244,234; and WO 91/00357.

Expression of heterologous genes in insects can be accomplished as described in U.S. Pat. No. 4,745,051; Friesen et al. (1986) "The Regulation of Baculovirus Gene Expression" in: THE MOLECULAR BIOLOGY OF BACULOVIRUSES (W. Doerfler, ed.); EP 127,839; EP 155,476; Vlak et al., *J. Gen. Virol*. (1988) 69: 765-776; Miller et al., *Ann. Rev. Microbiol*. (1988) 42: 177; Carbonell et al., *Gene* (1988) 73: 409; Maeda et al., *Nature* (1985) 315: 592-594; Lebacq-Verheyden et al., *Mol. Cell Biol*. (1988) 8: 3129; Smith et al., *Proc. Natl. Acad. Sci. USA* (1985) 82: 8404; Miyajima et al., *Gene* (1987) 58: 273; and Martin et al., *DNA* (1988) 7:99. Numerous baculoviral strains and variants and corresponding permissive insect host cells from hosts are described in Luckow et al., *Bio/Technology* (1988) 6: 47-55, Miller et al., in GENERIC ENGINEERING (Setlow, J. K. et al. eds.), Vol. 8 (Plenum Publishing, 1986), pp. 277-279; and Maeda et al., *Nature*, (1985), 315: 592-594.

Mammalian expression can be accomplished as described in Dijkema et al., *EMBO J*. (1985) 4: 761; Gormanetal., *Proc. Natl. Acad. Sci. USA* (1982b) 79: 6777; Boshart et al., *Cell* (1985) 41: 521; and U.S. Pat. No. 4,399,216. Other features of mammalian expression can be facilitated as described in Ham and Wallace, *Meth Enz*. (1979) 58: 44; Barnes and Sato, Anal. Biochem. (1980) 102: 255; U.S. Pat. No. 4,767,704; U.S. Pat. No. 4,657,866; U.S. Pat. No. 4,927,762; U.S. Pat. No. 4,560,655; WO 90/103430, WO 87/00195, and U.S. RE 30,985.

Expression constructs can be introduced into host cells using any technique known in the art. These techniques include transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and calcium phosphate-mediated transfection.

Expression of an endogenous gene encoding a protein of the invention can also be manipulated by introducing by homologous recombination a DNA construct comprising a transcription unit in frame with the endogenous gene, to form a homologously recombinant cell comprising the transcription unit. The transcription unit comprises a targeting sequence, a regulatory sequence, an exon, and an unpaired splice donor site. The new transcription unit can be used to turn the endogenous gene on or off as desired. This method of affecting endogenous gene expression is taught in U.S. Pat. No. 5,641,670.

The targeting sequence is a segment of at least 10, 12, 15, 20, or 50 contiguous nucleotides from the nucleotide sequence shown in FIG. 1 (SEQ ID NO:1). The transcription unit is located upstream to a coding sequence of the endogenous gene. The exogenous regulatory sequence directs transcription of the coding sequence of the endogenous gene.

BRCC2 can also include hybrid and modified forms of BRCC2 proteins including fusion proteins, BRCC2 fragments and hybrid and modified forms in which certain amino acids have been deleted or replaced, modifications such as where one or more amino acids have been changed to a modified amino acid or unusual amino acid, and modifications such as glycosylations so long as the hybrid or modified form retains at least one of the biological activities of BRCC2. By retaining the biological activity of BRCC2, it is meant that the protein modulates cancer cell proliferation or apoptosis, although not necessarily at the same level of potency as that of BRCC2 as described herein.

Also included within the meaning of substantially homologous is any BRCC2 which may be isolated by virtue of cross-reactivity with antibodies to the BRCC2 described herein or whose encoding nucleotide sequences including genomic DNA, mRNA or cDNA may be isolated through hybridization with the complementary sequence of genomic or subgenomic nucleotide sequences or cDNA of the BRCC2 herein or fragments thereof. It will also be appreciated by one skilled in the art that degenerate DNA sequences can encode human BRCC2 and these are also intended to be included within the present invention as are allelic variants of BRCC2.

Preferred BRCC2 of the present invention have been identified and isolated in purified form as described. Also preferred is BRCC2 prepared by recombinant DNA technology. By "pure form" or "purified form" or "substantially purified form" it is meant that a BRCC2 composition is substantially free of other proteins which are not BRCC2.

The present invention also includes therapeutic or pharmaceutical compositions comprising BRCC2 in an effective amount for treating patients with disease, and a method comprising administering a therapeutically effective amount of BRCC2. These compositions and methods are useful for treating a number of diseases including cancer. One skilled in the art can readily use a variety of assays known in the art to determine whether BRCC2 would be useful in promoting survival or functioning in a particular cell type.

In certain circumstances, it may be desirable to modulate or decrease the amount of BRCC2 expressed. Thus, in another aspect of the present invention, BRCC2 anti-sense oligonucleotides can be made and a method utilized for diminishing the level of expression of BRCC2 by a cell comprising administering one or more BRCC2 anti-sense oligonucleotides. By BRCC2 anti-sense oligonucleotides reference is made to oligonucleotides that have a nucleotide sequence that interacts through base pairing with a specific complementary nucleic acid sequence involved in the expression of BRCC2 such that the expression of BRCC2 is reduced. Preferably, the specific nucleic acid sequence involved in the expression of BRCC2 is a genomic DNA molecule or mRNA molecule that encodes BRCC2. This genomic DNA molecule can comprise regulatory regions of the BRCC2 gene, or the coding sequence for mature BRCC2 protein.

The term complementary to a nucleotide sequence in the context of BRCC2 antisense oligonucleotides and methods therefor means sufficiently complementary to such a sequence as to allow hybridization to that sequence in a cell, i.e., under physiological conditions. The BRCC2 antisense oligonucleotides preferably comprise a sequence containing from about 8 to about 100 nucleotides and more preferably the BRCC2 antisense oligonucleotides comprise from about 15 to about 30 nucleotides. The BRCC2 antisense oligonucleotides can also contain a variety of modifications that confer resistance to nucleolytic degradation such as, for example, modified internucleoside linages (Uhlmann and Peyman, *Chemical Reviews* 90:543-548 1990; Schneider and Banner, *Tetrahedron Lett.* 31:335, 1990 which are incorporated by reference), modified nucleic acid bases as disclosed in U.S. Pat. No. 5,958,773 and patents disclosed therein, and/or sugars and the like.

Any modifications or variations of the antisense molecule which are known in the art to be broadly applicable to antisense technology are included within the scope of the invention. Such modifications include preparation of phosphorus-containing linkages as disclosed in U.S. Pat. Nos. 5,536,821; 5,541,306; 5,550,111; 5,563,253; 5,571,799; 5,587,361, 5,625,050 and 5,958,773.

The antisense compounds of the invention can include modified bases. The antisense oligonucleotides of the invention can also be modified by chemically linking the oligonucleotide to one or more moieties or conjugates to enhance the activity, cellular distribution, or cellular uptake of the antisense oligonucleotide. Such moieties or conjugates include lipids such as cholesterol, cholic acid, thioether, aliphatic chains, phospholipids, polyamines, polyethylene glycol (PEG), palmityl moieties, and others as disclosed in, for example, U.S. Pat. Nos. 5,514,758, 5,565,552, 5,567,810, 5,574,142, 5,585,481, 5,587,371, 5,597,696 and 5,958,773.

Chimeric antisense oligonucleotides are also within the scope of the invention, and can be prepared from the present inventive oligonucleotides using the methods described in, for example, U.S. Pat. Nos. 5,013,830, 5,149,797, 5,403,711, 5,491,133, 5,565,350, 5,652,355, 5,700,922 and 5,958,773.

In the antisense art, a certain degree of routine experimentation is required to select optimal antisense molecules for particular targets. To be effective, the antisense molecule preferably is targeted to an accessible, or exposed, portion of the target RNA molecule. Although in some cases information is available about the structure of target mRNA molecules, the current approach to inhibition using antisense is via experimentation. mRNA levels in the cell can be measured routinely in treated and control cells by reverse transcription of the mRNA and assaying the cDNA levels. The biological effect can be determined routinely by measuring cell growth, proliferation or viability as is known in the art. Assays for measuring apoptosis are also known.

Measuring the specificity of antisense activity by assaying and analyzing cDNA levels is an art-recognized method of validating antisense results. It has been suggested that RNA from treated and control cells should be reverse-transcribed and the resulting cDNA populations analyzed. (Branch, A. D., *T.I.B.S.* 23:45-50, 1998.)

The therapeutic or pharmaceutical compositions of the present invention can be administered by any suitable route known in the art including for example intravenous, subcutaneous, intramuscular, transdermal, intrathecal or intracerebral. Administration can be either rapid as by injection or over a period of time as by slow infusion or administration of slow release formulation.

BRCC2 can also be linked or conjugated with agents that provide desirable pharmaceutical or pharmacodynamic properties. For example, BRCC2 can be coupled to any substance known in the art to promote penetration or transport across the blood-brain barrier such as an antibody to the transferrin receptor, and administered by intravenous injection (see, for example, Friden et al., *Science* 259:373-377, 1993 which is incorporated by reference). Furthermore, BRCC2 can be stably linked to a polymer such as polyethylene glycol to obtain desirable properties of solubility, stability, half-life and other pharmaceutically advantageous properties. (See, for example, Davis et al., *Enzyme Eng.* 4:169-73; 1978; Buruham, *Am. J. Hosp. Pharm.* 51:210-218, 1994 which are incorporated by reference.)

The compositions are usually employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous. BRCC2 can also be incorporated into a solid or semi-solid biologically compatible matrix which can be implanted into tissues requiring treatment.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically acceptable excipients for modifying or maintaining release or absorption or penetration across the blood-brain barrier. Such excipients are those substances usually and customarily employed to formulate dosages for parenteral administration in either unit dosage or multi-dose form or for direct infusion into the cerebrospinal fluid by continuous or periodic infusion.

Dose administration can be repeated depending upon the pharmacokinetic parameters of the dosage formulation and the route of administration used.

It is also contemplated that certain formulations containing BRCC2 are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid; sustained, or delayed release of the active ingredients after administration to the patient by employing procedures well known in the art. The formulations can also contain substances that diminish proteolytic degradation and promote absorption such as, for example, surface-active agents.

The specific dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

In one embodiment of this invention, BRCC2 may be therapeutically administered by implanting into patients vectors or cells capable of producing a biologically-active form of BRCC2 or a precursor of BRCC2, i.e., a molecule that can be readily converted to a biological-active form of BRCC2 by the body. In one approach cells that secrete BRCC2 may be encapsulated into semipermeable membranes for implantation into a patient. The cells can be cells that normally express BRCC2 or a precursor thereof or the cells can be transformed to express BRCC2 or a precursor thereof. It is preferred that the cell be of human origin and that the BRCC2 be human BRCC2 when the patient is human. However, the formulations and methods herein can be used for veterinary as well as human applications and the term "patient" as used herein is intended to include human and veterinary patients.

In a number of circumstances it would be desirable to determine the levels of BRCC2 in a patient. The identification of BRCC2 along with the present report showing expression of BRCC2 provides the basis for the conclusion that the presence of BRCC2 serves a normal physiological function related to cell growth and survival. Endogenously produced BRCC2 may also play a role in certain disease conditions.

The term "detection" as used herein in the context of detecting the presence of BRCC2 in a patient is intended to include the determining of the amount of BRCC2 or the ability to express an amount of BRCC2 in a patient, the estimation of prognosis in terms of probable outcome of a disease and prospect for recovery, the monitoring of the BRCC2 levels over a period of time as a measure of status of the condition, and the monitoring of BRCC2 levels for determining a preferred therapeutic regimen for the patient.

To detect the presence of BRCC2 in a patient, a sample is obtained from the patient. The sample can be a tissue biopsy sample or a sample of blood, plasma, serum, CSF or the like. BRCC2 tissue expression is disclosed in the examples. Samples for detecting BRCC2 can be taken from these tissue. When assessing peripheral levels of BRCC2, it is preferred that the sample be a sample of blood, plasma or serum. When assessing the levels of BRCC2 in the central nervous system a preferred sample is a sample obtained from cerebrospinal fluid or neural tissue.

In some instances it is desirable to determine whether the BRCC2 gene is intact in the patient or in a tissue or cell line within the patient. By an intact BRCC2 gene, it is meant that there are no alterations in the gene such as point mutations, deletions, insertions, chromosomal breakage, chromosomal rearrangements and the like wherein such alteration might alter production of BRCC2 or alter its biological activity, stability or the like to lead to disease processes. Thus, in one embodiment of the present invention a method is provided for detecting and characterizing any alterations in the BRCC2 gene. The method comprises providing an oligonucleotide that contains the BRCC2 cDNA, genomic DNA or a fragment thereof or a derivative thereof. By a derivative of an oligonucleotide, it is meant that the derived oligonucleotide is substantially the same as the sequence from which it is derived in that the derived sequence has sufficient sequence complementarily to the sequence from which it is derived to hybridize to the BRCC2 gene. The derived nucleotide sequence is not necessarily physically derived from the nucleotide sequence, but may be generated in any manner including for example, chemical synthesis or DNA replication or reverse transcription or transcription.

Typically, patient genomic DNA is isolated from a cell sample from the patient and digested with one or more restriction endonucleases such as, for example, TaqI and AluI. Using the Southern blot protocol, which is well known in the art, this assay determines whether a patient or a particular tissue in a patient has an intact BRCC2 gene or a BRCC2 gene abnormality.

Hybridization to a BRCC2 gene would involve denaturing the chromosomal DNA to obtain a single-stranded DNA; contacting the single-stranded DNA with a gene probe associated with the BRCC2 gene sequence; and identifying the hybridized DNA-probe to detect chromosomal DNA containing at least a portion of a human BRCC2 gene.

The term "probe" as used herein refers to a structure comprised of a polynucleotide that forms a hybrid structure with a target sequence, due to complementarity of probe sequence with a sequence in the target region. Oligomers suitable for use as probes may contain a minimum of about 8-12 contiguous nucleotides which are complementary to the targeted sequence and preferably a minimum of about 20.

The BRCC2 gene probes of the present invention can be DNA or RNA oligonucleotides and can be made by any method known in the art such as, for example, excision, transcription or chemical synthesis. Probes may be labeled with any detectable label known in the art such as, for example, radioactive or fluorescent labels or enzymatic marker. Labeling of the probe can be accomplished by any method known in the art such as by PCR, random priming, end labeling, nick translation or the like. One skilled in the art will also recognize that other methods not employing a labeled probe can be used to determine the hybridization. Examples of methods that can be used for detecting hybridization include Southern blotting, fluorescence in situ hybridization, and single-strand conformation polymorphism with PCR amplification.

Hybridization is typically carried out at 25°-45° C., more preferably at 32°-40° C. and more preferably at 37°-38° C. The time required for hybridization is from about 0.25 to about 96 hours, more preferably from about one to about 72 hours, and most preferably from about 4 to about 24 hours.

BRCC2 gene abnormalities can also be detected by using the PCR method and primers that flank or lie within the BRCC2 gene. The PCR method is well known in the art. Briefly, this method is performed using two oligonucleotide primers which are capable of hybridizing to the nucleic acid sequences flanking a target sequence that lies within a BRCC2 gene and amplifying the target sequence. The terms "olignucleotide primer" as used herein refers to a short strand of DNA or RNA ranging in length from about 8' to about 30 bases. The upstream and downstream primers are typically from about 20 to about 30 base pairs in length and hybridize to the flanking regions for replication of the nucleotide sequence. The polymerization is catalyzed by a DNA-polymerase in the presence of deoxynucleotide triphosphates or nucleotide analogs to produce double-stranded DNA molecules. The double strands are then separated by any denaturing method including physical, chemical or enzymatic. Commonly, a method of physical denaturation is used involving heating the nucleic acid, typically to temperatures from about 80° C. to 105° C. for times ranging from about 1 to about 10 minutes. The process is repeated for the desired number of cycles.

The primers are selected to be substantially complementary to the strand of DNA being amplified. Therefore, the primers need not reflect the exact sequence of the template, but must be sufficiently complementary to selectively hybridize with the strand being amplified.

After PCR amplification, the DNA sequence comprising BRCC2 or a fragment thereof is then directly sequenced and analyzed by comparison of the sequence with the sequences disclosed herein to identify alterations which might change activity or expression levels or the like.

In another embodiment, a method for detecting BRCC2 is provided based upon an analysis of tissue expressing the BRCC2 gene. Certain tissues such as those identified below in Example 6 and 7 have been found to express the BRCC2 gene. The method comprises hybridizing a polynucleotide to mRNA from a sample of tissue that normally expresses the BRCC2 gene. The sample is obtained from a patient suspected of having an abnormality in the BRCC2 gene or in the BRCC2 gene of particular cells.

To detect the presence of mRNA encoding BRCC2 protein, a sample is obtained from a patient. The sample can be from blood or from a tissue biopsy sample. The sample may be treated to extract the nucleic acids contained therein. The resulting nucleic acid from the sample is subjected to gel electrophoresis or other size, separation techniques.

The mRNA of the sample is contacted with a DNA sequence serving as a probe to form hybrid duplexes. The use of a labeled probes as discussed above allows detection of the resulting duplex.

When using the cDNA encoding BRCC2 protein or a derivative of the cDNA as a probe, high stringency conditions can be used in order to prevent false positives, that is the hybridization and apparent detection of BRCC2 nucleotide sequences when in fact an intact and functioning BRCC2 gene is not present. When using sequences derived from the BRCC2 cDNA, less stringent conditions could be used, however, this would be a less preferred approach because of the likelihood of false positives. The stringency of hybridization is determined by a number of factors during hybridization and during the washing procedure, including temperature, ionic strength, length of time and concentration of formamide. These factors are outlined in, for example, Sambrook et al. (Sambrook et al., 1989, supra).

In order to increase the sensitivity of the detection in a sample of mRNA encoding the BRCC2 protein, the technique of reverse transcription/polymerization chain reaction (RT/PCR) can be used to amplify cDNA transcribed from mRNA encoding the BRCC2 protein. The method of RT/PCR is well known in the art, and can be performed as follows. Total cellular RNA is isolated by, for example, the standard guanidium isothiocyanate method and the total RNA is reverse transcribed. The reverse transcription method involves synthesis of DNA on a template of RNA using a reverse transcriptase enzyme and a 3' end primer. Typically, the primer contains an oligo(dT) sequence. The cDNA thus produced is then amplified using the PCR method and BRCC2 specific primers. (Belyavsky et al., *Nucl. Acid Res.* 17:2919-2932, 1989; Krug and Berger, *Methods in Enzymology*, 152:316-325, Academic Press, NY, 1987 which are incorporated by reference).

The polymerase chain reaction method is performed as described above using two oligonucleotide primers that are substantially complementary to the two flanking regions of the DNA segment to be amplified. Following amplification, the PCR product is then electrophoresed and detected by ethidium bromide staining or by phosphoimaging.

The present invention further provides for methods to detect the presence of the BRCC2 protein in a sample obtained from a patient. Any method known in the art for detecting proteins can be used. Such methods include, but are not limited to immunodiffusion, immunoelectrophoresis, immunochemical methods, binder-ligand assays, immunohistochemical techniques, agglutination and complement assays. (*Basic and Clinical Immunology*, 217-262, Sites and Terr, eds., Appleton & Lange, Norwalk, Conn., 1991, which is incorporated by reference). Preferred are binder-ligand immunoassay methods including reacting antibodies with an epitope or epitopes of the BRCC2 protein and competitively displacing a labeled BRCC2 protein or derivative thereof.

As used herein, a derivative of the BRCC2 protein is intended to include a polypeptide in which certain amino acids have been deleted or replaced or changed to modified or unusual amino acids wherein the BRCC2 derivative is biologically equivalent to BRCC2 and wherein the polypeptide derivative cross-reacts with antibodies raised against the BRCC2 protein. By cross-reaction it is meant that an antibody reacts with an antigen other than the one that induced its formation.

Numerous competitive and non-competitive protein binding immunoassays are well known in the art. Antibodies employed in such assays may be unlabeled, for example as used in agglutination tests, or labeled for use in a wide variety of assay methods. Labels that can be used include radionuclides, enzymes, fluorescers, chemiluminescers, enzyme substrates or co-factors, enzyme inhibitors, particles, dyes and the like for use in radioinununoassay (RIA), enzyme immunoassays, e.g., enzyme-linked immunosorbent assay (ELISA), fluorescent immunoassays and the like.

Polyclonal or monoclonal antibodies to the protein or an epitope thereof can be made for use in immunoassays by any of a number of methods known in the art. By epitope reference is made to an antigenic determinant of a polypeptide. An epitope could comprise 3 amino acids in a spatial conformation which is unique to the epitope. Generally an epitope consists of at least 5 such amino acids. Methods of determining the spatial conformation of amino acids are known in the art, and include, for example, x-ray crystallography and 2 dimensional nuclear magnetic resonance.

One approach for preparing antibodies to a protein is the selection and preparation of an amino acid sequence of all or part of the protein, chemically synthesizing the sequence and injecting it into an appropriate animal, usually a rabbit or a mouse.

Oligopeptides can be selected as candidates for the production of an antibody to the BRCC2 protein based upon the oligopeptides lying in hydrophilic regions, which are thus likely to be exposed in the mature protein. Peptide sequence used to generate antibodies against any fragment of BRCC2 that typically is at least 5-6 amino acids in length, optionally fused to an immunogenic carrier protein, e.g. KLH or BSA.

Additional oligopeptides can be determined using, for example, the Antigenicity Index, Welling, G. W. et al., *FEBS Lett.* 188:215-218 (1985), incorporated herein by reference.

In other embodiments of the present invention, humanized monoclonal antibodies are provided, wherein the antibodies are specific for BRCC2. The phrase "humanized antibody" refers to an antibody derived from a non-human antibody, typically a mouse monoclonal antibody. Alternatively, a humanized antibody may be derived from a chimeric antibody that retains or substantially retains the antigen-binding properties of the parental, non-human, antibody but which exhibits diminished immunogenicity as compared to the parental antibody when administered to humans. The phrase "chimeric antibody," as used herein, refers to an antibody containing sequence derived from two different antibodies (see, e.g., U.S. Pat. No. 4,816,567) which typically originate from different species. Most typically, chimeric antibodies comprise human and murine antibody fragments, generally human constant and mouse variable regions.

Because humanized antibodies are far less immunogenic in humans than the parental mouse monoclonal antibodies, they can be used for the treatment of humans with far less risk of anaphylaxis. Thus, these antibodies may be preferred in therapeutic applications that involve in vivo administration to a human such as, e.g., use as radiation sensitizers for the treatment of neoplastic disease or use in methods to reduce the side effects of, e.g., cancer therapy.

Humanized antibodies may be achieved by a variety of methods including, for example: (1) grafting the non-human complementarity determining regions (CDRs) onto a human framework and constant region (a process referred to in the art as "humanizing"), or, alternatively, (2) transplanting the entire non-human variable domains, but "cloaking" them with a human-like surface by replacement of surface residues (a process referred to in the art as "veneering"). In the present invention, humanized antibodies will include both "humanized" and "veneered" antibodies. These methods are disclosed in, e.g., Jones et al., *Nature* 321:522-525 (1986); Morrison et al., *Proc. Natl. Acad. Sci, US.A.*, 81:6851-6855 (1984); Morrison and Oi, *Adv. Immunol.*, 44:65-92 (1988); Verhoeyer et al., *Science* 239:1534-1536 (1988); Padlan, *Molec. Immun.* 28:489-498 (1991); Padlan, *Molec. Immunol.* 31(3):169-217 (1994); and Kettleborough, C. A. et al., *Protein Eng.* 4(7):773-83 (1991) each of which is incorporated herein by reference.

The phrase "complementarity determining region" refers to amino acid sequences which together define the binding affinity and specificity of the natural Fv region of a native immunoglobulin binding site. See, e.g., Chothia et al., *J. Mol. Biol.* 196:901-917 (1987); Kabat et al., U.S. Dept. of Health and Human Services NIH Publication No. 91-3242 (1991). The phrase "constant region" refers to the portion of the antibody molecule that confers effector functions. In the present invention, mouse constant regions are substituted by human constant regions. The constant regions of the subject humanized antibodies are derived from human immunoglobulins. The heavy chain constant region can be selected from any of the five isotypes: alpha, delta, epsilon, gamma or mu.

One method of humanizing antibodies comprises aligning the non-human heavy and light chain sequences to human heavy and light chain sequences, selecting and replacing the non-human framework with a human framework based on such alignment, molecular modeling to predict the conformation of the humanized sequence and comparing to the conformation of the parent antibody. This process is followed by repeated back mutation of residues in the CDR region which disturb the structure of the CDRs until the predicted conformation of the humanized sequence model closely approximates the conformation of the non-human CDRs of the parent non-human antibody. Such humanized antibodies may be further derivatized to facilitate uptake and clearance, e.g, via Ashwell receptors. See, e.g., U.S. Pat. Nos. 5,530,101 and 5,585,089 which patents are incorporated herein by reference.

Humanized antibodies to BRCC2 can also be produced using transgenic animals that are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/10741 also discloses transgenic non-primate mammalian hosts capable of mounting an immune response to an immunogen, wherein the antibodies have primate constant and/or variable regions, and wherein the endogenous immunoglobulin-encoding loci are substituted or inactivated. WO 96/30498 discloses the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy claims, and express an exogenous immunoglobulin locus comprising one or more xenogeneic constant regions.

Using a transgenic animal described above, an immune response can be produced to a selected antigenic molecule, and antibody-producing cells can be removed from the animal and used to produce hybridomas that secrete human monoclonal antibodies. Immunization protocols, adjuvants, and the like are known in the art, and are used in immunization of, for example, a transgenic mouse as described in WO 96/33735. This publication discloses monoclonal antibodies against a variety of antigenic molecules including IL-6, IL-8, TNF, human CD4, L-selectin, gp39, and tetanus toxin. The monoclonal antibodies can be tested for the ability to inhibit or neutralize the biological activity or physiological effect of the corresponding protein. WO 96/33735 discloses that monoclonal antibodies against IL-8, derived from immune cells of transgenic mice immunized with IL-8, blocked IL-8-induced functions of neutrophils. Human monoclonal antibodies with specificity for the antigen used to immunize transgenic animals are also disclosed in WO 96/34096.

In the present invention, BRCC2 polypeptides of the invention and variants thereof are used to immunize a transgenic animal as described above. Monoclonal antibodies are made using methods known in the art, and the specificity of the antibodies is tested using isolated BRCC2 polypeptides.

Methods for preparation of the BRCC2 protein or an epitope thereof include, but are not limited to chemical synthesis, recombinant DNA techniques or isolation from biological samples. Chemical synthesis of a peptide can be performed, for example, by the classical Merrifeld method of solid phase peptide synthesis (Merrifeld, *J. Am. Chem. Soc.* 85:2149, 1963 which is incorporated by reference) or the FMOC strategy on a Rapid Automated Multiple Peptide Synthesis system (E. I. du Pont de Nemours Company, Wilmington, Del.) (Caprino and Han, *J. Org. Chem.* 37:3404, 1972 which is incorporated by reference).

Polyclonal antibodies can be prepared by immunizing rabbits or other animals by injecting antigen followed by subsequent boosts at appropriate intervals. The animals are bled and sera assayed against purified BRCC2 protein usually by ELISA or by bioassay based upon the ability to block the action of BRCC2. In a non-limiting example, an antibody to BRCC2 can block the binding of BRCC2 to Disheveled protein. When using avian species, e.g., chicken, turkey and the like, the antibody can be isolated from the yolk of the egg. Monoclonal antibodies can be prepared after the method of Milstein and Kohler by fusing splenocytes from immunized mice with continuously replicating tumor cells such as myeloma or lymphoma cells. (Milstein and Kohler, *Nature* 256:495-497, 1975; Gulfre and Milstein, *Methods in Enzymology: Immunochemical Techniques* 73:1-46, Langone and Banatis eds., Academic Press, 1981 which are incorporated by reference). The hybridoma cells so formed are then cloned by limiting dilution methods and supernates assayed for antibody production by ELISA, RIA or bioassay.

The unique ability of antibodies to recognize and specifically bind to target proteins provides an approach for treating an overexpression of the protein. Thus, another aspect of the present invention provides for a method for preventing or treating diseases involving overexpression of the BRCC2 protein by treatment of a patient with specific antibodies to the BRCC2 protein.

Specific antibodies, either polyclonal or monoclonal, to the BRCC2 protein can be produced by any suitable method known in the art as discussed above. For example, murine or human monoclonal antibodies can be produced by hybridoma technology or, alternatively, the BRCC2 protein, or an immunologically active fragment thereof, or an anti-idiotypic antibody, or fragment thereof can be administered to an animal to elicit the production of antibodies capable of recognizing and binding to the BRCC2 protein. Such antibodies can be from any class of antibodies including, but not limited to IgG, IgA, IgM, IgD, and IgE or in the case of avian species, IgY and from any subclass of antibodies.

The availability of BRCC2 allows for the identification of small molecules and low molecular weight compounds that inhibit the binding of BRCC2 to binding partners, through routine application of high-throughput screening methods (HTS). HTS methods generally refer to technologies that permit the rapid assaying of lead compounds for therapeutic potential. HTS techniques employ robotic handling of test materials, detection of positive signals, and interpretation of data. Lead compounds may be identified via the incorporation of radioactivity or through optical assays that rely on absorbence, fluorescence or luminescence as read-outs. Gonzalez, J. E. et al., (1998) *Curr. Opin. Biotech.* 9:624-631.

Model systems are available that can be adapted for use in high throughput screening for compounds that inhibit the interaction of BRCC2 with its ligand, for example by competing with BRCC2 for ligand binding. Sarubbi et al., (1996) *Anal. Biochem.* 237:70-75 describe cell-free, non-isotopic assays for discovering molecules that compete with natural ligands for binding to the active site of IL-1 receptor. Martens, C. et al., (1999) *Anal. Biochem.* 273:20-31 describe a generic particle-based nonradioactive method in which a labeled ligand binds to its receptor immobilized on a particle; label on the particle decreases in the presence of a molecule that competes with the labeled ligand for receptor binding.

The therapeutic BRCC2 polynucleotides and polypeptides of the present invention may be utilized in gene delivery vehicles. The gene delivery vehicle may be of viral or non-viral origin (see generally, Jolly, *Cancer Gene Therapy* 1:51-64 (1994); Kimura, *Human Gene Therapy* 5:845-852 (1994); Connelly, *Human Gene Therapy* 1:185-193 (1995); and Kaplitt, *Nature Genetics* 6:148-153 (1994)). Gene therapy vehicles for delivery of constructs including a coding sequence of a therapeutic of the invention can be administered either locally or systemically. These constructs can utilize viral or non-viral vector approaches. Expression of such coding sequences can be induced using endogenous mammalian or heterologous promoters. Expression of the coding sequence can be either constitutive or regulated.

The present invention can employ recombinant retroviruses which are constructed to carry or express a selected nucleic acid molecule of interest. Retrovirus vectors that can be employed include those described in EP 0 415 731; WO 90/0793 6; WO 94/03622; WO 93/25698; WO 93/25234; U.S. Pat. No. 5,219,740; WO 93/11230; WO 93/10218; Vile and Hart, *Cancer Res.* 53:3860-3864 (1993); Vile and Hart, *Cancer Res.* 53:962-967 (1993); Ram et al., *Cancer Res.* 53:83-88 (1993); Takamiya et al., *J. Neurosci. Res.* 33:493-503 (1992); Baba et al., *J. Neurosurg.* 79:729-735 (1993); U.S. Pat. No. 4,777,127; GB Patent No. 2,200,651; and EP 0 345 242. Preferred recombinant retroviruses include those described in WO 91/02805.

Packaging cell lines suitable for use with the above-described retroviral vector constructs may be readily prepared (see PCT publications WO 95/3 0763 and WO 92/05266), and used to create producer cell lines (also termed vector cell lines) for the production of recombinant vector particles. Within particularly preferred embodiments of the invention, packaging cell lines are made from human (such as HT1080 cells) or mink parent cell lines, thereby allowing production of recombinant retroviruses that can survive inactivation in human serum.

The present invention also employs alphavirus-based vectors that can function as gene delivery vehicles. Such vectors can be constructed from a wide variety of alphaviruses, including, for example, Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532). Representative examples of such vector systems include those described in U.S. Pat. Nos. 5,091,309; 5,217,879; and 5,185,440; and PCT Publication Nos. WO 92/10578; WO 94/21792; WO 95/27069; WO 95/27044; and WO 95/07994.

Gene delivery vehicles of the present invention can also employ parvovirus such as adeno-associated virus (AAV) vectors. Representative examples include the AAV vectors disclosed by Srivastava in WO 93/09239, Samulski et al., *J. Vir.* 63:3822-3828 (1989); Mendelson et al., *Virol.* 166:154-165 (1988); and Flotte et al., *P.N.A.S.* 90:10613-10617 (1993).

Representative examples of adenoviral vectors include those described by Berkner, *Biotechniques* 6:616-627 (Biotechniques); Rosenfeld et al., *Science* 252:431-434 (1991); WO 93/19191; Kolls et al., P.N.A.S. 215-219 (1994); Kass-Bisleret al., P.N.A.S. 90:11498-11502 (1993); Guzman et al., *Circulation* 88:2838-2848 (1993); Guzman et al., *Cir. Res.* 73:1202-1207 (1993); Zabner et al., *Cell* 75:207-216 (1993); Li et al., *Hum. Gene Ther.* 4:403-409 (1993); Cailaud et al., *Eur. J. Neurosci.* 5:1287-1291 (1993); Vincent et al., *Nat. Genet.* 5:130-134 (1993); Jaffe et al., *Nat. Genet.* 1:372-378 (1992); and Levrero et al., *Gene* 101:195-202 (1992). Exemplary adenoviral gene therapy vectors employable in this invention also include those described in WO 94/12649, WO 93/03769; WO 93/19191; WO 94/28938; WO 95/11984 and WO 95/00655. Administration of DNA linked to killed adenovirus as described in Curiel, *Hum. Gene Ther.* 3:147-154.(1992) may be employed.

Other gene delivery vehicles and methods may be employed, including polycationic condensed DNA linked or unlinked to killed adenovirus alone, for example Curiel, *Hum. Gene Ther.* 3:147-154 (1992); ligand-linked DNA, for example see Wu, *J. Biol. Chem.* 264:16985-16987 (1989); eukaryotic cell delivery vehicles cells; deposition of photopolymerized hydrogel materials; hand-held gene transfer particle gun, as described in U.S. Pat. No. 5,149,655; ionizing radiation as described in U.S. Pat. No. 5,206,152 and in WO 92/11033; nucleic charge neutralization or fusion with cell membranes. Additional approaches are described in Philip, *Mol. Cell Biol.* 14:2411-2418 (1994), and in Woffendin, *Proc. Natl. Acad. Sci.* 91:1581-1585 (1994).

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm. Liposomes that can act as gene delivery vehicles are described in U.S. Pat. No. 5,422,120, PCT Patent Publication Nos. WO 95/13 796, WO 94/23697, and WO 9 1/14445, and EP No. 0 524 968.

Further non-viral delivery suitable for use includes mechanical delivery systems such as the approach described in Woffendin et al., *Proc. Natl. Acad. Sci. USA* 91(24): 11581-11585 (1994). Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and PCT Patent Publication No. WO 92/11033.

BRCC2 may also be used in screens to identify drugs for treatment of cancers which involve over-activity of the encoded protein, or new targets which would be useful in the identification of new drugs.

For all of the preceding embodiments, the clinician will determine, based on the specific condition, whether BRCC2 polypeptides or polynucleotides, antibodies to BRCC2, or small molecules such as peptide analogues or antagonists, will be the most suitable form of treatment. These forms are all within the scope of the invention.

The present invention has been described with reference to specific embodiments. However, this invention is intended to cover those changes and substitutions, which may be made by those skilled in the art without departing from the spirit and scope of the appended claims.

What is claimed is:

1. An isolated nucleic acid molecule comprising a polynucleotide selected from the group consisting of:
   (a) a polynucleotide encoding the amino acid sequence of SEQ ID NO: 2; and
   (b) the polynucleotide complement of the polynucleotide of (a).

2. The isolated nucleic acid molecule of claim 1, which is DNA.

3. A recombinant vector comprising the nucleic acid molecule of claim 1 in operable linkage to a promoter.

4. A recombinant host cell comprising the recombinant vector of claim 3.

* * * * *